(12) United States Patent
Gilham et al.

(10) Patent No.: US 9,384,652 B2
(45) Date of Patent: *Jul. 5, 2016

(54) SYSTEM AND METHOD FOR TRANSFER OF PRIMARY ALARM NOTIFICATION ON PATIENT MONITORING SYSTEMS

(71) Applicant: Spacelabs Healthcare LLC, Snoqualmie, WA (US)

(72) Inventors: Jeffrey Jay Gilham, Sammamish, WA (US); Patrick Scott Jensen, Sammamish, WA (US)

(73) Assignee: SPACELABS HEALTHCARE, LLC, Snoqualmie, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/460,147

(22) Filed: Aug. 14, 2014

(65) Prior Publication Data

US 2015/0035679 A1 Feb. 5, 2015

Related U.S. Application Data

(63) Continuation of application No. 13/300,434, filed on Nov. 18, 2011, now Pat. No. 8,842,001.

(60) Provisional application No. 61/415,799, filed on Nov. 19, 2010.

(51) Int. Cl.
G08B 13/14 (2006.01)
G08B 25/00 (2006.01)
(Continued)

(52) U.S. Cl.
CPC .............. *G08B 25/005* (2013.01); *A61B 5/002* (2013.01); *A61B 5/746* (2013.01); *G06F 19/3418* (2013.01); *G08B 21/02* (2013.01); *A61B 5/0205* (2013.01)

(58) Field of Classification Search
None
See application file for complete search history.

(56) References Cited

U.S. PATENT DOCUMENTS 2,820,651 A 1/1958 Phillips
2,912,858 A 11/1959 Fuller
(Continued)

FOREIGN PATENT DOCUMENTS

CN 1688256 10/2005
CN 1781107 A 5/2006
(Continued)

OTHER PUBLICATIONS

International Search Report for PCT/US2011/61557, Apr. 23, 2012.
(Continued)

*Primary Examiner* — Julie Lieu
(74) *Attorney, Agent, or Firm* — Novel IP (57) ABSTRACT

The present application discloses methods and systems for transferring primary alarm notification on patient monitoring systems from a bedside monitor to one or more secondary devices which may operate on a less than fully reliable network. The bedside monitor includes an attached physiological parameter measurement device which detects when a specific physiological parameter measures outside a predetermined range. The bedside monitor then directs the secondary device(s) to annunciate its alarm. Primary alarming responsibility reverts from the secondary device(s) back to the bedside monitor whenever communication between the two is lost or when acknowledgement of the alarm condition by the secondary device is not relayed back to the bedside monitor within a predetermined amount of time.

20 Claims, 5 Drawing Sheets (51) Int. Cl.
*A61B 5/00* (2006.01)
*G06F 19/00* (2011.01)
*G08B 21/02* (2006.01)
*A61B 5/0205* (2006.01)

(56) References Cited

U.S. PATENT DOCUMENTS

| | | |
|---|---|---|
| 2,944,547 A | 7/1960 | Ziherl |
| 3,517,639 A | 6/1970 | Whitsel |
| 3,608,545 A | 9/1971 | Novack |
| 3,618,592 A | 11/1971 | Stewart |
| 3,673,863 A | 7/1972 | Spacek |
| 3,897,606 A | 8/1975 | Schleining |
| 3,938,551 A | 2/1976 | Henkin |
| 3,981,329 A | 9/1976 | Wohlwend |
| 4,064,826 A | 12/1977 | Pauli |
| 4,148,312 A | 4/1979 | Bird |
| 4,167,115 A | 9/1979 | Stoever |
| 4,513,294 A | 4/1985 | Anderson |
| 4,557,216 A | 12/1985 | Demyon |
| 4,625,731 A | 12/1986 | Quedens |
| 4,630,486 A | 12/1986 | Miles |
| 4,697,450 A | 10/1987 | Bachman |
| 4,869,253 A | 9/1989 | Craig |
| 4,879,997 A | 11/1989 | Bickford |
| 4,903,222 A | 2/1990 | Carter |
| 4,944,305 A | 7/1990 | Takatsu |
| 4,991,576 A | 2/1991 | Henkin |
| 5,087,906 A | 2/1992 | Eaton |
| 5,101,851 A | 4/1992 | Abadi |
| 5,144,898 A | 9/1992 | Posly |
| 5,197,480 A | 3/1993 | Gebhardt |
| 5,213,108 A | 5/1993 | Bredesen |
| 5,222,486 A | 6/1993 | Vaughn |
| 5,231,981 A | 8/1993 | Schreiber |
| 5,233,975 A | 8/1993 | Choate |
| 5,262,944 A | 11/1993 | Weisner |
| 5,291,182 A | 3/1994 | Wiseman |
| 5,311,908 A | 5/1994 | Barone |
| 5,319,363 A | 6/1994 | Welch |
| 5,322,069 A | 6/1994 | Gallant |
| 5,331,549 A | 7/1994 | Crawford, Jr. |
| 5,333,106 A | 7/1994 | Lanpher |
| 5,339,826 A | 8/1994 | Schmidt |
| 5,348,008 A | 9/1994 | Bornn |
| 5,372,389 A | 12/1994 | Tam |
| 5,373,746 A | 12/1994 | Bloss |
| 5,419,332 A | 5/1995 | Sabbah |
| 5,438,983 A | 8/1995 | Falcone |
| 5,467,954 A | 11/1995 | Wekell |
| 5,473,536 A | 12/1995 | Wimmer |
| 5,482,050 A | 1/1996 | Smokoff |
| 5,497,766 A | 3/1996 | Foster |
| 5,502,853 A | 4/1996 | Singleton |
| 5,515,083 A | 5/1996 | Casebolt |
| 5,553,296 A | 9/1996 | Forrest |
| 5,558,418 A | 9/1996 | Lambright |
| 5,563,495 A | 10/1996 | Tomiyori |
| 5,584,291 A | 12/1996 | Vapola |
| 5,586,909 A | 12/1996 | Saba |
| 5,633,457 A | 5/1997 | Kilar |
| 5,682,526 A | 10/1997 | Smokoff |
| 5,684,504 A | 11/1997 | Verhulst |
| 5,687,717 A | 11/1997 | Halpern |
| 5,692,494 A | 12/1997 | Pernetti |
| 5,715,813 A | 2/1998 | Guevrekian |
| 5,718,235 A | 2/1998 | Golosarsky |
| 5,724,025 A | 3/1998 | Tavori |
| 5,724,985 A | 3/1998 | Snell |
| 5,749,367 A | 5/1998 | Gamlyn |
| 5,752,917 A | 5/1998 | Fuchs |
| 5,765,842 A | 6/1998 | Phaneuf |
| 5,779,305 A | 7/1998 | Hocking |
| 5,787,298 A | 7/1998 | Broedner |
| 5,800,360 A | 9/1998 | Kisner |
| 5,800,387 A | 9/1998 | Duffy |
| 5,819,741 A | 10/1998 | Karlsson |
| 5,855,550 A | 1/1999 | Lai |
| 5,868,133 A | 2/1999 | DeVries |
| 5,904,328 A | 5/1999 | Leveridge |
| 5,956,013 A | 9/1999 | Raj |
| 5,975,081 A | 11/1999 | Hood |
| 6,005,767 A | 12/1999 | Ku |
| 6,024,089 A | 2/2000 | Wallace |
| 6,042,548 A | 3/2000 | Giuffre |
| 6,048,044 A | 4/2000 | Biggel |
| 6,050,940 A | 4/2000 | Braun |
| 6,063,028 A | 5/2000 | Luciano |
| 6,096,025 A | 8/2000 | Borders |
| 6,099,093 A | 8/2000 | Spence |
| 6,131,571 A | 10/2000 | Lampotang |
| 6,134,537 A | 10/2000 | Pao |
| 6,146,523 A | 11/2000 | Kenley |
| 6,155,255 A | 12/2000 | Lambert |
| 6,269,813 B1 | 8/2001 | Fitzgerald |
| 6,322,502 B1 | 11/2001 | Schoenberg |
| 6,338,823 B1 | 1/2002 | Furukawa |
| 6,339,732 B1 | 1/2002 | Phoon |
| 6,347,310 B1 | 2/2002 | Passera |
| 6,383,136 B1 | 5/2002 | Jordan |
| 6,396,583 B1 | 5/2002 | Clare |
| 6,424,860 B1 | 7/2002 | Karlsson |
| 6,435,690 B1 | 8/2002 | Till |
| 6,443,889 B1 | 9/2002 | Groth |
| D467,001 S | 12/2002 | Buczek |
| 6,488,029 B1 | 12/2002 | Hood |
| 6,536,430 B1 | 3/2003 | Smith |
| 6,554,238 B1 | 4/2003 | Hibberd |
| 6,571,227 B1 | 5/2003 | Agrafiotis |
| 6,571,792 B1 | 6/2003 | Hendrickson |
| 6,591,694 B2 | 7/2003 | Tsai |
| 6,600,662 B1 | 7/2003 | Emmert |
| 6,647,341 B1 | 11/2003 | Golub |
| 6,650,779 B2 | 11/2003 | Vachtesvanos |
| 6,674,837 B1 | 1/2004 | Taskar |
| 6,692,258 B1 | 2/2004 | Kurzweil |
| 6,692,436 B1 | 2/2004 | Bluth |
| 6,699,187 B2 | 3/2004 | Webb |
| 6,702,754 B2 | 3/2004 | Ogura |
| 6,715,722 B2 | 4/2004 | Roberts |
| 6,735,648 B2 | 5/2004 | Onishi |
| 6,771,172 B1 | 8/2004 | Robinson |
| 6,804,656 B1 | 10/2004 | Rosenfeld |
| 6,824,539 B2 | 11/2004 | Novak |
| 6,829,501 B2 | 12/2004 | Nielsen |
| 6,931,795 B1 | 8/2005 | Baloga |
| 6,933,931 B2 | 8/2005 | Lubarsky, Jr. |
| 6,985,762 B2 | 1/2006 | Brashears |
| 7,006,865 B1 | 2/2006 | Cohen |
| 7,013,833 B2 | 3/2006 | Lemberger |
| 7,024,569 B1 | 4/2006 | Wright |
| 7,031,857 B2 | 4/2006 | Tarassenko |
| 7,038,588 B2 | 5/2006 | Boone |
| 7,076,435 B1 | 7/2006 | McKeag |
| 7,081,091 B2 | 7/2006 | Merrett |
| RE39,233 E | 8/2006 | McGrath |
| 7,096,864 B1 | 8/2006 | Mayer |
| 7,111,852 B2 | 9/2006 | Woods |
| 7,117,438 B2 | 10/2006 | Wallace |
| 7,128,709 B2 | 10/2006 | Saruya |
| 7,137,951 B2 | 11/2006 | Pilarski |
| 7,193,233 B2 | 3/2007 | Smith |
| 7,216,802 B1 | 5/2007 | De La Huerga |
| 7,223,007 B1 | 5/2007 | Fredley |
| 7,234,944 B2 | 6/2007 | Nordin |
| 7,256,708 B2 * | 8/2007 | Rosenfeld ............ G06F 19/325 340/539.12 |
| 7,265,676 B2 | 9/2007 | Gordon |
| 7,267,666 B1 | 9/2007 | Duchon |
| 7,282,029 B1 | 10/2007 | Poulsen |
| 7,315,825 B2 | 1/2008 | Rosenfeld |
| 7,336,980 B1 | 2/2008 | Kaikuranta |
| 7,360,454 B2 | 4/2008 | Kawashima |
| 7,371,214 B2 | 5/2008 | Kouchi |

(56) References Cited

U.S. PATENT DOCUMENTS

| | | |
|---|---|---|
| 7,386,340 B2 | 6/2008 | Schlegel |
| 7,468,032 B2 | 12/2008 | Stahmann |
| 7,469,601 B2 | 12/2008 | Sugi |
| 7,489,250 B2 | 2/2009 | Bock |
| D589,959 S | 4/2009 | Han |
| 7,516,924 B2 | 4/2009 | White |
| 7,523,040 B2 | 4/2009 | Kirchhoff |
| 7,529,083 B2 | 5/2009 | Jeong |
| 7,540,187 B1 | 6/2009 | Dillon |
| 7,566,307 B2 | 7/2009 | Inukai |
| 7,621,500 B2 | 11/2009 | Ishizaki |
| 7,751,878 B1 | 7/2010 | Merkle |
| 7,756,722 B2 | 7/2010 | Levine |
| 7,836,882 B1 | 11/2010 | Rumph |
| 7,945,452 B2 | 5/2011 | Fathallah |
| 7,974,924 B2 | 7/2011 | Holla |
| 8,002,701 B2 | 8/2011 | John |
| 8,027,846 B2 | 9/2011 | Schoenberg |
| 8,033,686 B2 | 10/2011 | Recker |
| 8,147,419 B2 | 4/2012 | Krauss |
| 8,190,900 B2 | 5/2012 | Corndorf |
| 8,233,272 B2 | 7/2012 | Fidacaro |
| 8,273,018 B1 * | 9/2012 | Fackler .................. G08B 7/066 128/903 |
| 8,344,847 B2 | 1/2013 | Moberg |
| 8,398,408 B1 | 3/2013 | Hansen |
| 8,413,271 B2 | 4/2013 | Blanchard |
| 8,593,275 B2 | 11/2013 | Davis |
| 8,704,666 B2 | 4/2014 | Baker, Jr. |
| 8,798,527 B2 | 8/2014 | Gaines |
| 8,811,888 B2 | 8/2014 | Wiesner |
| 8,818,260 B2 | 8/2014 | Gaines |
| 8,855,550 B2 | 10/2014 | Gaines |
| 8,868,028 B1 | 10/2014 | Kaltsukis |
| 8,897,198 B2 | 11/2014 | Gaines |
| 8,903,308 B2 | 12/2014 | Wiesner |
| 8,922,330 B2 | 12/2014 | Moberg |
| 8,931,702 B2 | 1/2015 | Wekell |
| 8,940,147 B1 | 1/2015 | Bartsch |
| 8,943,168 B2 | 1/2015 | Wiesner |
| 9,020,419 B2 | 4/2015 | Gaines |
| 2001/0001179 A1 | 5/2001 | Healy |
| 2001/0018332 A1 | 8/2001 | Lustila |
| 2001/0027791 A1 | 10/2001 | Wallace |
| 2001/0034475 A1 | 10/2001 | Flach |
| 2002/0026941 A1 | 3/2002 | Biondi |
| 2002/0032386 A1 | 3/2002 | Sackner |
| 2002/0060247 A1 | 5/2002 | Krishnaswamy |
| 2002/0108011 A1 | 8/2002 | Tanha |
| 2002/0161291 A1 | 10/2002 | Kianl |
| 2002/0173991 A1 | 11/2002 | Avitall |
| 2002/0193679 A1 | 12/2002 | Malave |
| 2002/0196141 A1 | 12/2002 | Boone |
| 2002/0196234 A1 | 12/2002 | Gray |
| 2003/0028118 A1 | 2/2003 | Dupree |
| 2003/0029451 A1 | 2/2003 | Blair |
| 2003/0037786 A1 | 2/2003 | Biondi |
| 2003/0065536 A1 | 4/2003 | Hansen |
| 2003/0076015 A1 | 4/2003 | Ehrenreich |
| 2003/0114836 A1 | 6/2003 | Estes |
| 2003/0117296 A1 | 6/2003 | Seely |
| 2003/0120164 A1 | 6/2003 | Nielsen |
| 2003/0130590 A1 | 7/2003 | Bui |
| 2003/0135087 A1 | 7/2003 | Hickle |
| 2003/0145854 A1 | 8/2003 | Hickle |
| 2003/0171898 A1 | 9/2003 | Tarassenko |
| 2003/0191373 A1 | 10/2003 | Blike |
| 2003/0197614 A1 | 10/2003 | Smith |
| 2003/0209246 A1 | 11/2003 | Schroeder |
| 2003/0210780 A1 | 11/2003 | Pratt |
| 2003/0216621 A1 | 11/2003 | Alpert |
| 2003/0231460 A1 | 12/2003 | Moscovitch |
| 2003/0233129 A1 | 12/2003 | Matos |
| 2004/0011938 A1 | 1/2004 | Oddsen |
| 2004/0015079 A1 | 1/2004 | Berger |
| 2004/0021705 A1 | 2/2004 | Baker |
| 2004/0024303 A1 | 2/2004 | Banks |
| 2004/0032426 A1 | 2/2004 | Rutledge |
| 2004/0054261 A1 | 3/2004 | Kamataki |
| 2004/0054295 A1 | 3/2004 | Ramseth |
| 2004/0102687 A1 | 5/2004 | Brashears |
| 2004/0103001 A1 | 5/2004 | Mazar |
| 2004/0116813 A1 | 6/2004 | Selzer |
| 2004/0117209 A1 | 6/2004 | Brown |
| 2004/0118404 A1 | 6/2004 | Wallace |
| 2004/0147818 A1 | 7/2004 | Levy |
| 2004/0149892 A1 | 8/2004 | Akitt |
| 2004/0153257 A1 | 8/2004 | Munk |
| 2004/0158132 A1 | 8/2004 | Zaleski |
| 2004/0172222 A1 | 9/2004 | Simpson |
| 2004/0186357 A1 | 9/2004 | Soderberg |
| 2004/0220629 A1 | 11/2004 | Kamath |
| 2004/0221077 A1 | 11/2004 | Yen |
| 2004/0236192 A1 | 11/2004 | NecolaShehada |
| 2004/0249298 A1 | 12/2004 | Selevan |
| 2004/0249673 A1 | 12/2004 | Smith |
| 2005/0005932 A1 | 1/2005 | Berman |
| 2005/0010165 A1 | 1/2005 | Hickle |
| 2005/0033124 A1 | 2/2005 | Kelly |
| 2005/0033188 A1 | 2/2005 | Whitaker |
| 2005/0038332 A1 | 2/2005 | Saidara |
| 2005/0038821 A1 | 2/2005 | Wallen |
| 2005/0054920 A1 | 3/2005 | Washburn |
| 2005/0059924 A1 | 3/2005 | Katz |
| 2005/0065417 A1 | 3/2005 | Ali |
| 2005/0113650 A1 | 5/2005 | Pacione |
| 2005/0124866 A1 | 6/2005 | Elaz |
| 2005/0139213 A1 | 6/2005 | Blike |
| 2005/0146431 A1 | 7/2005 | Hastings |
| 2005/0148890 A1 | 7/2005 | Hastings |
| 2005/0151640 A1 | 7/2005 | Hastings |
| 2005/0177096 A1 | 8/2005 | Bollish |
| 2005/0229110 A1 | 10/2005 | Gegner |
| 2005/0251232 A1 | 11/2005 | Hartley |
| 2006/0004475 A1 | 1/2006 | Brackett |
| 2006/0022096 A1 | 2/2006 | Chan |
| 2006/0042635 A1 | 3/2006 | Niklewski |
| 2006/0058591 A1 | 3/2006 | Garboski |
| 2006/0094970 A1 | 5/2006 | Drew |
| 2006/0142808 A1 | 6/2006 | Pearce |
| 2006/0155206 A1 | 7/2006 | Lynn |
| 2006/0155589 A1 | 7/2006 | Lane |
| 2006/0161295 A1 | 7/2006 | Yun |
| 2006/0199618 A1 | 9/2006 | Steer |
| 2006/0226992 A1 | 10/2006 | Al-Ali |
| 2006/0258926 A1 | 11/2006 | Ali |
| 2006/0280621 A1 | 12/2006 | Kinugawa |
| 2006/0282302 A1 | 12/2006 | Hussain |
| 2007/0007418 A1 | 1/2007 | Lubbers |
| 2007/0028921 A1 | 2/2007 | Banner |
| 2007/0032749 A1 | 2/2007 | Overall |
| 2007/0044578 A1 | 3/2007 | Jones |
| 2007/0050715 A1 | 3/2007 | Behar |
| 2007/0051861 A1 | 3/2007 | Teramachi |
| 2007/0060869 A1 | 3/2007 | Tolle |
| 2007/0093784 A1 | 4/2007 | Leonard |
| 2007/0100213 A1 | 5/2007 | Dossas |
| 2007/0107728 A1 | 5/2007 | Ricciardelli |
| 2007/0108291 A1 | 5/2007 | Bhatia |
| 2007/0120763 A1 | 5/2007 | DePaepe |
| 2007/0176931 A1 | 8/2007 | Tivig |
| 2007/0180140 A1 | 8/2007 | Welch |
| 2007/0199388 A1 | 8/2007 | Furkert |
| 2007/0199566 A1 | 8/2007 | Be |
| 2007/0255116 A1 | 11/2007 | Mehta |
| 2007/0265533 A1 | 11/2007 | Tran |
| 2007/0276277 A1 | 11/2007 | Booth |
| 2008/0033254 A1 | 2/2008 | Kamath |
| 2008/0039701 A1 | 2/2008 | Ali |
| 2008/0039735 A1 | 2/2008 | Hickerson |
| 2008/0051667 A1 | 2/2008 | Goldreich |
| 2008/0077435 A1 * | 3/2008 | Muradia .............. G06F 19/3418 705/2 |
| 2008/0103375 A1 | 5/2008 | Kiani |

(56) References Cited

U.S. PATENT DOCUMENTS

| | | | |
|---|---|---|---|
| 2008/0117029 A1* | 5/2008 | Dohrmann | G08B 25/001 340/286.02 |
| 2008/0154909 A1 | 6/2008 | Dam | |
| 2008/0167569 A1 | 7/2008 | Ermes | |
| 2008/0170287 A1 | 7/2008 | Champion | |
| 2008/0177160 A1 | 7/2008 | Al Ali | |
| 2008/0177397 A1 | 7/2008 | Davlin | |
| 2008/0181465 A1 | 7/2008 | Sauerwein | |
| 2008/0221418 A1 | 9/2008 | Al-Ali | |
| 2008/0221495 A1 | 9/2008 | Steffens | |
| 2008/0228045 A1 | 9/2008 | Gao | |
| 2008/0228089 A1 | 9/2008 | Cho | |
| 2008/0249376 A1 | 10/2008 | Zaleski | |
| 2008/0251003 A1 | 10/2008 | Boston | |
| 2008/0267790 A1 | 10/2008 | Gaudet | |
| 2008/0271736 A1 | 11/2008 | Leonard | |
| 2008/0275309 A1 | 11/2008 | Stivoric | |
| 2008/0281168 A1 | 11/2008 | Gibson | |
| 2008/0281170 A1 | 11/2008 | Eshelman | |
| 2008/0287763 A1 | 11/2008 | Hayter | |
| 2008/0294057 A1 | 11/2008 | Parlikar | |
| 2008/0310600 A1 | 12/2008 | Clawson | |
| 2008/0319331 A1 | 12/2008 | Zizzo | |
| 2009/0005703 A1 | 1/2009 | Fasciano | |
| 2009/0015116 A1 | 1/2009 | Arceta | |
| 2009/0024008 A1 | 1/2009 | Brunner | |
| 2009/0054743 A1 | 2/2009 | Stewart | |
| 2009/0055735 A1 | 2/2009 | Zaleski | |
| 2009/0069642 A1 | 3/2009 | Gao | |
| 2009/0076345 A1 | 3/2009 | Manicka | |
| 2009/0099480 A1 | 4/2009 | Salgo | |
| 2009/0117784 A1 | 5/2009 | Wu | |
| 2009/0124239 A1 | 5/2009 | Tsuei | |
| 2009/0131805 A1 | 5/2009 | OBrien | |
| 2009/0133609 A1 | 5/2009 | Nethken | |
| 2009/0149901 A1* | 6/2009 | Jayne | A61N 1/39 607/3 |
| 2009/0151720 A1 | 6/2009 | Inoue | |
| 2009/0182204 A1 | 7/2009 | Semler | |
| 2009/0192541 A1 | 7/2009 | Ortiz | |
| 2009/0193315 A1 | 7/2009 | Gower | |
| 2009/0200902 A1 | 8/2009 | McKay | |
| 2009/0206713 A1 | 8/2009 | Vilkas | |
| 2009/0209849 A1 | 8/2009 | Rowe | |
| 2009/0237264 A1 | 9/2009 | Bobey | |
| 2009/0326340 A1 | 12/2009 | Wang | |
| 2010/0004539 A1 | 1/2010 | Chen | |
| 2010/0007588 A1 | 1/2010 | Zygmunt | |
| 2010/0014229 A1 | 1/2010 | Horie | |
| 2010/0056875 A1 | 3/2010 | Schoenberg | |
| 2010/0070417 A1 | 3/2010 | Flynn | |
| 2010/0073915 A1 | 3/2010 | Nittou | |
| 2010/0094096 A1 | 4/2010 | Petruzzelli | |
| 2010/0110019 A1 | 5/2010 | Ozias | |
| 2010/0137729 A1 | 6/2010 | Pierry | |
| 2010/0164452 A1 | 7/2010 | Ruan | |
| 2010/0175695 A1 | 7/2010 | Jamison | |
| 2010/0179400 A1 | 7/2010 | Brauker | |
| 2010/0233891 A1 | 9/2010 | Broeksteeg | |
| 2010/0238138 A1 | 9/2010 | Goertz | |
| 2010/0259881 A1 | 10/2010 | Choi | |
| 2010/0261979 A1 | 10/2010 | Kiani | |
| 2010/0285771 A1 | 11/2010 | Peabody | |
| 2010/0294405 A1 | 11/2010 | Longinotti-Buitoni | |
| 2010/0298656 A1 | 11/2010 | McCombie | |
| 2010/0298718 A1 | 11/2010 | Gilham | |
| 2010/0318578 A1 | 12/2010 | Treu | |
| 2010/0324380 A1 | 12/2010 | Perkins | |
| 2010/0324384 A1 | 12/2010 | Moon | |
| 2010/0324936 A1 | 12/2010 | Vishnubhatla | |
| 2011/0004071 A1 | 1/2011 | Faiola | |
| 2011/0071420 A1 | 3/2011 | Pierre | |
| 2011/0077971 A1 | 3/2011 | Surwit | |
| 2011/0087756 A1 | 4/2011 | Biondi | |
| 2011/0088694 A1 | 4/2011 | Tobia | |
| 2011/0125040 A1 | 5/2011 | Crawford | |
| 2011/0130798 A1 | 6/2011 | Elghazzawi | |
| 2011/0138323 A1 | 6/2011 | Skidmore | |
| 2011/0152629 A1 | 6/2011 | Eaton | |
| 2011/0164074 A1 | 7/2011 | Frank | |
| 2011/0190643 A1 | 8/2011 | Zhang | |
| 2011/0225771 A1 | 9/2011 | Bartnick | |
| 2011/0245579 A1 | 10/2011 | Bruggeman | |
| 2011/0257489 A1 | 10/2011 | Banet | |
| 2011/0279383 A1 | 11/2011 | Wilson | |
| 2011/0279958 A1 | 11/2011 | Clark | |
| 2012/0030610 A1 | 2/2012 | DiPerna | |
| 2012/0041786 A1 | 2/2012 | Yu | |
| 2012/0075060 A1* | 3/2012 | Connor | G06F 19/327 340/5.54 |
| 2012/0075327 A1 | 3/2012 | Mackenzie | |
| 2012/0093311 A1* | 4/2012 | Nierzwick | H04L 9/0838 380/255 |
| 2012/0095778 A1 | 4/2012 | Gross | |
| 2012/0105233 A1 | 5/2012 | Bobey | |
| 2012/0105774 A1 | 5/2012 | Fletcher | |
| 2012/0127103 A1 | 5/2012 | Qualey | |
| 2012/0209984 A1 | 8/2012 | Gonzalez-Banos | |
| 2012/0232398 A1 | 9/2012 | Roham | |
| 2012/0233679 A1* | 9/2012 | Shedrinsky | G06F 19/327 726/7 |
| 2012/0330675 A1* | 12/2012 | Muradia | G06F 19/3418 705/2 |
| 2013/0015966 A1 | 1/2013 | Soomro | |
| 2013/0162426 A1 | 6/2013 | Wiesner | |
| 2013/0267861 A1 | 10/2013 | Vassallo | |
| 2014/0153747 A1 | 6/2014 | Contolini | |
| 2015/0018703 A1* | 1/2015 | Shetty | A61B 5/7435 600/531 |

FOREIGN PATENT DOCUMENTS

| | | |
|---|---|---|
| CN | 1943505 A | 4/2007 |
| CN | 1983258 A | 6/2007 |
| CN | 101194278 | 6/2008 |
| DE | 9415672 | 11/1994 |
| DE | 102006011151 | 9/2007 |
| EP | 0686900 A2 | 12/1995 |
| EP | 0955007 A1 | 11/1999 |
| EP | 1054338 | 11/2000 |
| EP | 1227752 A1 | 5/2001 |
| EP | 1852060 | 11/2007 |
| EP | 1868123 A1 | 12/2007 |
| EP | 2555668 A2 | 2/2013 |
| EP | 2805564 A4 | 9/2015 |
| GB | 191214095 | 0/1912 |
| GB | 568212 | 3/1945 |
| GB | 2389290 A | 12/2003 |
| JP | 07163527 | 6/1995 |
| JP | 2003210422 | 7/2003 |
| WO | 9415523 | 7/1994 |
| WO | 9918705 | 4/1999 |
| WO | 03091841 | 11/2003 |
| WO | 03102850 | 12/2003 |
| WO | 2004038669 A1 | 5/2004 |
| WO | 2005101276 A3 | 10/2005 |
| WO | 2005114524 A3 | 12/2005 |
| WO | 2006094055 A2 | 9/2006 |
| WO | 2010126916 | 11/2010 |
| WO | 2010126916 A1 | 11/2010 |
| WO | 2011001302 A1 | 1/2011 |
| WO | 2011046636 A1 | 4/2011 |
| WO | 2011047363 A1 | 4/2011 |
| WO | 2011119512 A1 | 9/2011 |
| WO | 2012068564 A2 | 5/2012 |
| WO | 2012068565 A2 | 5/2012 |
| WO | 2012068567 | 5/2012 |
| WO | 2012068568 A2 | 5/2012 |
| WO | 2012083276 A2 | 6/2012 |
| WO | 2012083281 A1 | 6/2012 |
| WO | 2012125135 A1 | 9/2012 |
| WO | 2012128808 A2 | 9/2012 |
| WO | 2012158720 A1 | 11/2012 |
| WO | 2013056171 A2 | 4/2013 |

(56) References Cited

FOREIGN PATENT DOCUMENTS

| WO | 2013173520 A2 | 11/2013 |
|---|---|---|
| WO | 2013173521 A2 | 11/2013 |
| WO | 2014055660 A1 | 4/2014 |
| WO | 2014194193 | 12/2014 |

OTHER PUBLICATIONS

International Search Report for PCT/US2011/061554, Feb. 14, 2014.
International Search Report for PCT/US2011/061555, Apr. 17, 2012.
International Search Report for PCT/US2011/061558, Aug. 10, 2012.
International Preliminary Report on Patentability for PCT/US2011/061554, Feb. 25, 2014.
Office Action for Chinese Patent Application No. 201080057413.3, Oct. 10, 2015.
Office Action dated Oct. 2, 2015 for U.S. Appl. No. 14/044,524.
Office Action for Chinese Patent Application No. 2011800707731, Sep. 29, 2015.
Office Action for Chinese Patent Application No. 2011800655173, May 15, 2015.
Chinese Office Action, Patent Application No. 201180025170X, Issued Apr. 21, 2014, First OA.
European Search Report for EP12786443.7, Apr. 15, 2015.
Extended European Search Report, EP 11861868.5, Sep. 28, 2015.
First Office Action, Chinese Patent Application No. 201180067543.X, Jun. 2014.
First Office Action, Chinese Patent Application No. 2012800351488, Jun. 13, 2015.
IntelliVue Patient Monitor; MP20/30, MP40/50, MP60/70/80/90, Release G.0 with Software Revision G.0x.xx (Philips) Sep. 2008; pp. 4, 10, 19, 20, 46-49, 82, 326, 348, 420, 422, 424, 452; Accessed on Sep. 30, 2013: <http://www.mc.vanderbilt.edu/documents/nursingeducationresources/files/MP20-MP90%20Instructions%20for%20Use%20Manual%20Rev_G_0%20%20English%20M8000-9001K.pdf>.
International Preliminary Report on Patentability, PCT/US12/38000, Nov. 13, 2013.
International Preliminary Report on Patentability, PCT/US2006/007269, Sep. 11, 2007, Spacelabs Medical.
International Preliminary Report on Patentability, PCT/US2011/028007, Sep. 17, 2013, International Search Authority.
International Preliminary Report on Patentability, PCT/US2011/065678, Jun. 18, 2013, International Search Authority.
International Preliminary Report on Patentability, PCT/US2011/065685, Jun. 18, 2013.
International Search Report, PCT/US2011/028007, Jul. 11, 2011, International Search Authority.
International Search Report, PCT/US2011/065685, May 8, 2012, International Search Authority.
International Search Report for PCT/US06/07269, Aug. 28, 2006.
International Search Report for PCT/US10/32635, Jul. 23, 2010.
International Search Report for PCT/US10/34025, Aug. 9, 2010.
International Search Report for PCT/US12/38000, Oct. 23, 2012.
International Search Report for PCT/US2010/052977, Mar. 18, 2011.
International Search Report for PCT/US2011/029278, Aug. 2, 2011.
International Search Report for PCT/US2011/065676, Sep. 20, 2012.
International Search Report for PCT/US2011/065678, Jun. 29, 2012.
International Search Report for PCT/US2012/060125, Apr. 19, 2013.
International Search Report for PCT/US2013/041246, Dec. 9, 2013.
International Search Report for PCT/US2013/041247, Jan. 10, 2014.
International Search Report for PCT/US2013/063087, Mar. 6, 2014.
International Search Report for PCT/US2014/040225, Nov. 5, 2014.
Notice of Allowance dated Jan. 28, 2015 for U.S. Appl. No. 13/300,478.
Notice of Allowance dated Jan. 8, 2015 for U.S. Appl. No. 13/329,259.
Notice of Allowance dated Mar. 13, 2015 for U.S. Appl. No. 12/906,081.
Notice of Allowance dated May 11, 2015 for U.S. Appl. No. 13/300,462.
Notice of Allowance dated May 27, 2015 for U.S. Appl. No. 14/165,193.
Notice of Allowance dated Nov. 18, 2015 for U.S. Appl. No. 14/557,135.
Notice of Allowance dated Oct. 31, 2014 for U.S. Appl. No. 12/114,689.
Notice of Allowance dated Sep. 3, 2014 for U.S. Appl. No. 13/973,862.
Office Action dated Apr. 16, 2015 for U.S. Appl. No. 14/557,135.
Office Action dated Apr. 24, 2015 for U.S. Appl. No. 13/651,337.
Office Action dated Apr. 7, 2015 for U.S. Appl. No. 13/472,332.
Office Action dated Aug. 1, 2011 for U.S. Appl. No. 11/716,513.
Office Action dated Aug. 14, 2014 for U.S. Appl. No. 12/768,714.
Office Action dated Aug. 28, 2009 for U.S. Appl. No. 11/716,513.
Office Action dated Aug. 4, 2015 for U.S. Appl. No. 13/329,219.
Office Action dated Aug. 6, 2015 for U.S. Appl. No. 13/045,539.
Office Action dated Dec. 10, 2014 for U.S. Appl. No. 14/165,193.
Office Action dated Feb. 26, 2015 for U.S. Appl. No. 12/768,714.
Office Action dated Jan. 17, 2013 for U.S. Appl. No. 12/768,714.
Office Action dated Jul. 2, 2012 for U.S. Appl. No. 11/716,513.
Office Action dated Jul. 2, 2015 for U.S. Appl. No. 13/895,527.
Office Action dated Jun. 18, 2012 for U.S. Appl. No. 12/768,714.
Office Action dated Jun. 18, 2015 for U.S. Appl. No. 13/329,186.
Office Action dated Mar. 23, 2010 for U.S. Appl. No. 11/716,513.
Office Action dated May 21, 2015 for U.S. Appl. No. 13/300,526.
Office Action Dated May 31, 2013 for U.S. Appl. No. 13/052,883.
Office Action dated Nov. 12, 2014 for U.S. Appl. No. 13/300,462.
Office Action dated Nov. 13, 2015 for U.S. Appl. No. 13/472,332.
Office Action dated Nov. 21, 2013 for U.S. Appl. No. 12/768,714.
Office Action dated Nov. 21, 2014 for U.S. Appl. No. 13/045,539.
Office Action dated Oct. 7, 2015 for U.S. Appl. No. 12/768,714.
Office Action dated Sep. 22, 2014 for U.S. Appl. No. 13/329,186.
Partial European Search Report for EP 12839321.2, May 26, 2015.
Schoenberg, Roy, MD; Sands, Daniel Z., MD MPH; Safran, Charles, MD; Center for Clinical Computing, Beth Israel Deaconess Medical Center, Harvard Medical School, "Making ICU Alarms Meaningful: a comparison of traditional vs. trend-based algorithms" (AMIA '99 Annual Symposium), 1999, pp. 1-5.
Second Office Action, Chinese Patent Application No. 201180025170X, Issued Jun. 7, 2015.
Supplemental Notice of Allowance dated Apr. 20, 2015 for U.S. Appl. No. 12/906,081.
Supplementary European Search Report, Nov. 25, 2009, Spacelabs Medical, PCT/US2006/007269.

* cited by examiner

SYSTEM AND METHOD FOR TRANSFER OF PRIMARY ALARM NOTIFICATION ON PATIENT MONITORING SYSTEMS

CROSS-REFERENCE TO RELATED APPLICATIONS

The present application is a continuation of U.S. patent application Ser. No. 13/300,434, filed on Nov. 18, 2011, which, in turn, claims priority from U.S. Provisional Patent Application No. 61/415,799, entitled "Patient Monitoring System with Dual Serial Bus (DSB) Interface" and filed on Nov. 19, 2010, all of which are herein incorporated by reference in their entirety.

FIELD

This specification relates generally to hospital-based patient monitoring systems. More particularly, the present specification relates to a system and method for transferring primary alarm notification from the patient bedside monitor to remote secondary devices in a cost-effective, fail-safe manner.

BACKGROUND

A patient monitoring system is an electronic medical device that measures a patient's various vital signs, collects and processes all measurements as data, and then displays the data graphically and/or numerically on a viewing screen. Graphical data is displayed continuously as data channels on a time axis (waveforms). In addition, a graphical user interface is often included to provide staff with access to change configuration and alarm limit settings. Patient monitoring systems are positioned near hospital beds, typically in critical care units, where they continually monitor patient status via measuring devices attached to the patient and can be viewed by hospital personnel. The systems are typically on a shelf, attached to the bed, or attached to a wall. Some patient monitoring systems can only be viewed on a local display, whereas others can be joined to a network and thereby display data at other locations, such as central monitoring or clinicians' stations.

Portable patient monitoring systems are available for use by emergency medical services (EMS) personnel. These systems typically include a defibrillator along with the monitor. Other portable units, such as Holter monitors, are worn by patients for a particular time period and then returned to the physician for evaluation of the measured and collected data. Current patient monitoring systems are able to measure and display a variety of vital signs, including, pulse oximetry ($SpO_2$), electrocardiograph (ECG), invasive blood pressure (IBP), non-invasive blood pressure (NIBP), electroencephalograph (EEG), body temperature, cardiac output, capnography ($CO_2$), and respiration. Patient monitoring systems are capable of measuring and displaying maximum, minimum, and average values and frequencies, such as pulse and respiratory rates.

Data collected can be transmitted through fixed wire connections or wireless data communication. Power to patient monitoring systems can be supplied through a main power line or by batteries. While current patient monitoring systems are effective in monitoring patient conditions and notifying medical personnel of changes, they are not without certain drawbacks and limitations.

Patient monitoring systems are typically equipped with audio and visual alarms to notify medical personnel of changes in the patient's status. The alarm parameters are typically set by medical personnel. For example, audible alarms can often be too loud and distracting to other patients, personnel and even family members that may be present in the patient's room. Bright, flashing visual clinician/nurse alarms can also be distracting to other patients. Conversely, more subtle visual alarms can be too difficult to visualize, which can be a result of visual clutter on the monitoring system display or because the visual alarm is not differentiated enough from other information on the display. In addition, it can be difficult for clinicians to silence an active alarm, delaying care to the patient. The typical user interface for alarm control is operated via traditional push-buttons or in many instances a touchscreen or keyboard.

Therefore, a need exists for a better alarm mechanism within patient monitoring systems, in which both the audible and visual alarms are easily recognized by the clinicians while not disturbing patients. In addition, there is a need for an alarm mechanism in which an attending clinician can quickly silence the alarm and then focus on the patient's needs.

In addition, although visual and audible alarms are generated in an alarm situation, there is seldom nursing staff dedicated to watching these systems as the nursing staff is busy attending to many patients. System-generated alarms next to the patient will often wake the patient, are often "false" alarms, and are also frightening to the patient's family. It is desirable to have the primary alarming notification occur at the location of the assigned caregiver, not at the patient, since it is the caregiver that needs to take action. One conventional method for providing alarm notifications at the caregiver location is to repeat information from patient monitors located at the patient's bedside within central work stations or send the information to pagers to alert staff of an alarm situation, specifically for when the staff is not physically in the patient's room. However, in these redundant systems, the alarm notification is often still present at the bedside and still has the drawback of disturbing patients and their families.

Another conventional method involves telemetry transmitters, which have no primary alarm capabilities and always transfer alarm notifications to a secondary device for primary alarming. Unfortunately, these systems require extensive and expensive equipment to ensure reliable transfer of primary alarming function.

Yet another conventional method involves a dedicated network specifically for patient monitoring. These networks are designed for maximum redundancy, reliability, and robustness in order to guarantee the transmission of alarm notifications. Such parallel monitoring networks are expensive, however, and not suitable for budget conscious hospitals or in global geographic regions lacking the ability to purchase and support a complex IT infrastructure.

Therefore, a need exists for a cost-effective, fail-safe method of sending primary alarm notifications from a patient monitor to a secondary device carried by one or more assigned caregivers, instead of sounding at the patient, and without requiring a discrete and dedicated network infrastructure. In particular, there is a need for a cost-effective, fail-safe method of sending primary alarm notifications from a patient monitor to a secondary device carried by one or more assigned caregivers which runs on a healthcare provider's existing network, even where that existing network is not completely reliable.

SUMMARY

In one embodiment, the present specification is directed towards a volatile or non-volatile computer readable medium, not including transmission media for transmitting waves, wherein said medium comprises: a first plurality of programmatic instructions, wherein, when executed by a first computing device, said first plurality of programmatic instructions: transmit a message from the first computing device to a second computing device wherein said message is a request to have the first computing device assume primary responsibility for annunciating an alarm; establish and maintain a heartbeat, wherein said heartbeat provides a consistent confirmation that a communication link between the first computing device and second computing device is operational; receive data indicative of an alarm state from the second computing device; and in response to receiving said data indicative of an alarm state from the second computing device, transmit an acknowledgement from the first computing device to the second computing device; and a second plurality of programmatic instructions, wherein, when executed by the second computing device, said second plurality of programmatic instructions: receives said message from the first computing device; in response to receiving said message, establish and maintain said heartbeat; monitor said heartbeat to confirm that a communication link between the first computing device and second computing device is operational; transmit said data indicative of an alarm state; suspend executing programmatic routines for annunciating an alarm in response to the alarm state if said acknowledgement from the first computing device is received; and cause said alarm to be annunciated in response to the alarm state based on said data indicative of an alarm state and said heartbeat status.

In one embodiment, the computing device is a bedside monitor.

In one embodiment, the first computing device is at least one of a cellular phone, PDA, smart phone, tablet computing device, patient monitor, custom kiosk, or other computing device capable of executing programmatic instructions.

In one embodiment, the second plurality of programmatic instructions cause said alarm to be annunciated at the second computing device in response to an alarm state if said heartbeat is not detected. In addition, the second plurality of programmatic instructions cause said alarm to be annunciated at the second computing device in response to an alarm state if said heartbeat fails to meet a predefined reliability threshold. Further, the second plurality of programmatic instructions does not cause said alarm to be annunciated at the second computing device if the heartbeat is detected and if the acknowledgement is received from the first computing device.

In one embodiment, the first plurality of programmatic instructions generates a user prompt to acknowledge receipt of an alarm message at said first computing device; receives user input in response to said prompt to acknowledge receipt of an alarm message; and transmits data indicative of said user input to the second computing device. Further, the second plurality of programmatic instructions does not cause said alarm to be annunciated at the second computing device if the heartbeat is detected, if the acknowledgement is received, and if data indicative of said user input is received. Still further, the second plurality of programmatic instructions does cause said alarm to be annunciated at the second computing device if any one of the following occurs: the heartbeat is not detected, the acknowledgement is not received, or data indicative of said user input is not received.

In one embodiment, the first plurality of programmatic instructions receives said data indicative of an alarm state from the second computing device, said first plurality of programmatic instructions cause an alarm to be annunciated at the first computing device.

In another embodiment, the present specification is directed towards a volatile or non-volatile computer readable medium, not including transmission media for transmitting waves, wherein said medium comprises: a first plurality of programmatic instructions, wherein, when executed by a first computing device, said first plurality of programmatic instructions: receives a message from a bedside monitor wherein said message is a request to have the first computing device assume primary responsibility for annunciating an alarm; in response to receiving said message, establish and maintain a heartbeat, wherein said heartbeat provides a consistent confirmation that a communication link between the first computing device and the bedside monitor is operational; receive data indicative of an alarm state from the bedside monitor; and in response to receiving said data indicative of an alarm state from the bedside monitor, transmit an acknowledgement from the first computing device to the bedside monitor; and a second plurality of programmatic instructions, wherein, when executed by the bedside monitor, said second plurality of programmatic instructions: transmit said message from the first computing device; establish and maintain said heartbeat; monitor said heartbeat to confirm that a communication link between the first computing device and bedside monitor is operational; transmit said data indicative of an alarm state; suspend executing programmatic routines for annunciating an alarm in response to the alarm state if said acknowledgement from the first computing device is received; and cause said alarm to be annunciated in response to the alarm state based on said data indicative of an alarm state and heartbeat status.

In one embodiment, the first computing device is at least one of a cellular phone, PDA, smart phone, tablet computing device, patient monitor, custom kiosk, or other computing device capable of executing programmatic instructions.

In one embodiment, the second plurality of programmatic instructions cause said alarm to be annunciated at the bedside monitor in response to an alarm state if said heartbeat is not detected. Further, the second plurality of programmatic instructions cause said alarm to be annunciated at the bedside monitor in response to an alarm state if the heartbeat fails to meet a predefined reliability threshold. Still further, the second plurality of programmatic instructions does not cause said alarm to be annunciated at the bedside monitor if the heartbeat is detected and if the acknowledgement is received from the first computing device.

In one embodiment, the first plurality of programmatic instructions generates a user prompt to acknowledge receipt of an alarm message at said first computing device; receives user input in response to said prompt to acknowledge receipt of an alarm message; and transmits data indicative of said user input to the bedside monitor. In addition, the second plurality of programmatic instructions does not cause said alarm to be annunciated at the bedside monitor if the heartbeat is detected, if the acknowledgement is received, and if data indicative of said user input is received. Further, the second plurality of programmatic instructions does cause said alarm to be annunciated at the bedside monitor if any one of the following occurs: the heartbeat is not detected, the acknowledgement is not received, or data indicative of said user input is not received.

In one embodiment, the first plurality of programmatic instructions receives said data indicative of an alarm state from the bedside monitor, said first plurality of programmatic instructions cause an alarm to be annunciated at the first computing device.

The aforementioned and other embodiments of the present specification shall be described in greater depth in the drawings and detailed description provided below.

BRIEF DESCRIPTION OF THE DRAWINGS

These and other features and advantages will be further appreciated, as they become better understood by reference to the detailed description when considered in connection with the accompanying drawings.

DETAILED DESCRIPTION

In one embodiment, the present specification discloses systems and methods for transferring primary alarm notification from the bedside patient monitoring system to secondary devices in a cost-effective, fail-safe manner.

In one embodiment, the present invention comprises a first computing device, such as a secondary alarming device capable of generating both audible and visual alarm notifications during an alarm condition, wherein the first computing device executes a first plurality of programmatic instructions; a second computing device, such as a physiological parameter measurement device running an embedded algorithm capable of generating both audible and visual alarm notifications during an alarm condition (i.e. low heart rate), wherein the second computing device executes a second plurality of programmatic instructions; a means of transferring data between said first and second computing devices; and a protocol designed to determine alarm notification hierarchy between said first and second computing devices.

In one embodiment, the present invention is comprised of the following: a physiological parameter measurement device running an embedded algorithm capable of generating both audible and visual alarm notifications during an alarm condition (i.e. low heart rate); one or more secondary alarming devices also capable of generating both audible and visual alarm notifications during an alarm condition; a means of transferring data between said physiological parameter measurement device and said secondary devices; and, a protocol designed to determine alarm notification hierarchy between said devices.

The at least one first computing device is capable of receiving primary alarm responsibility from the second computing device. Therefore, the physiological parameter measurement device of the present invention has the capability of transferring primary alarm notification responsibility to at least one secondary device. The at least one secondary device is carried by one or more assigned caregivers or positioned at fixed locations. This serves to lower the incidence of alarm related disturbances at the bedside and allows for increased efficiency of hospital personnel as the audible and visual alarms are only activated on the secondary devices.

In one embodiment, the system of the present invention is "fail-safe" in that it assumes that the network between the first computing device and second computing device, i.e. the secondary devices and bedside monitor, respectively, may be faulty or intermittent. Thus, while the bedside monitor has the ability to transfer primary alarming responsibility to one or more secondary alarming devices on the network, it will always revert to becoming the primary alarming device if a "heartbeat" and/or specific acknowledgement criteria are not received from the secondary devices. Therefore, the bedside monitor remains the primary alarming device if the heartbeat between the bedside monitor and the secondary device fails to meet a pre-defined reliability threshold. If there is an intermittent "heartbeat" or an unreliable connection, the system will cease communication with the secondary device. In one embodiment, the system determines the number of connection interruptions and assesses whether the connection environment is reliable enough to allow a secondary device to assume alarm responsibility, based upon a pre-defined connection interruption threshold. In one embodiment, the number of acceptable connection interruptions or the connection interruption threshold is pre-programmed by the user at the bedside monitor. In another embodiment, the number of acceptable connection interruptions is pre-programmed at the point of manufacture and cannot be changed.

Upon transfer of primary alarming responsibility to the at least one secondary device, the bedside monitor, in one embodiment, suspends executing programmatic routines for annunciating an alarm. Thus, in one embodiment, when an acknowledgement is received, local bedside monitor alarm conditions are suppressed. If, at any point, communication between devices fails or an acknowledgement is not received, the alarm routine(s) residing at the bedside monitor are unsuppressed or activated and the bedside monitor continues to execute programmatic routines for alarm annunciation.

In another embodiment, the secondary device acts as a redundant alarming device and also alarms when the primary device or bedside monitor alarms. Thus, alarm conditions, in one optional embodiment, are never suppressed at the bedside monitor. This allows a caregiver to monitor patients remotely, but also notifies a caregiver that may be present in the room of an alarm condition. In this case, an alarm may be acknowledged by using any device.

The present specification discloses multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
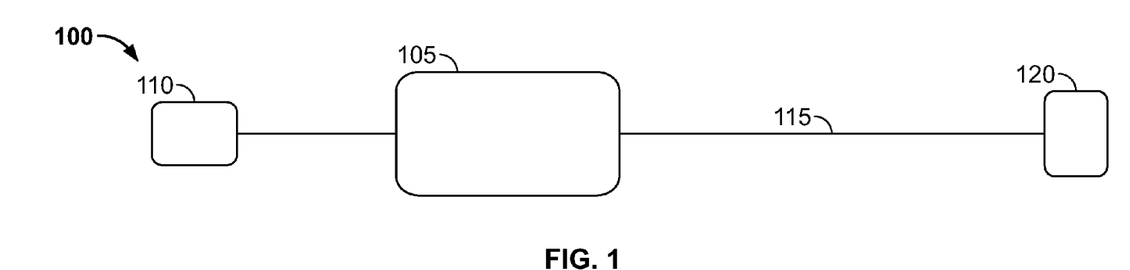
FIG. 1 is a block diagram illustrating one exemplary embodiment of the alarm priority system, depicting a bedside monitor with physiological parameter measurement device and one secondary alarming device.

FIG. 1 is a block diagram illustrating one exemplary embodiment of the alarm priority system 100 of the present invention, depicting a first computing device 120, such as a secondary alarming device, and a second computing device, such as, but not limited to bedside monitor 105 further including a physiological parameter measurement device.

In one embodiment, a physiological parameter measurement device 110 attached to a bedside monitor 105 executes an embedded algorithm capable of generating both audible and visual alarm notifications during an alarm condition. Physiological parameter measurement device 110 and bedside monitor 105 comprise conventional, standard standalone or networked monitoring systems. The physiological parameter measurement device 110 measures a patient parameter and notifies the bedside monitor 105 if said parameter falls outside of a normal range, signifying an alarm condition.

If primary alarm responsibility has been transferred to a secondary device 120, said secondary device 120 will then activate its audible and visual alarms and the bedside monitor 105 will remain silent.

Secondary alarming device 120 includes at least one of the following devices: a cellular phone, PDA, smartphone, tablet, other patient monitor, custom kiosk and/or any other computing device.

Communication between the bedside monitor 105 and the secondary device 120 is maintained via a network connection 115. In one embodiment, data is transferred between the bedside monitor and the secondary device via a wired network. In another embodiment, data is transferred between the bedside monitor and the secondary device via a wireless network such as 802.11 a/b/g/n, Bluetooth, or other protocol or standard. In another embodiment, data is transferred between the bedside monitor and the secondary device via a cellular network.

It should further be appreciated that each secondary device and monitoring system have wireless and wired receivers and transmitters capable of sending and transmitting data, at least one processor capable of processing programmatic instructions, memory capable of storing programmatic instructions, and software comprised of a plurality of programmatic instructions for performing the processes described herein.

Figure 2:
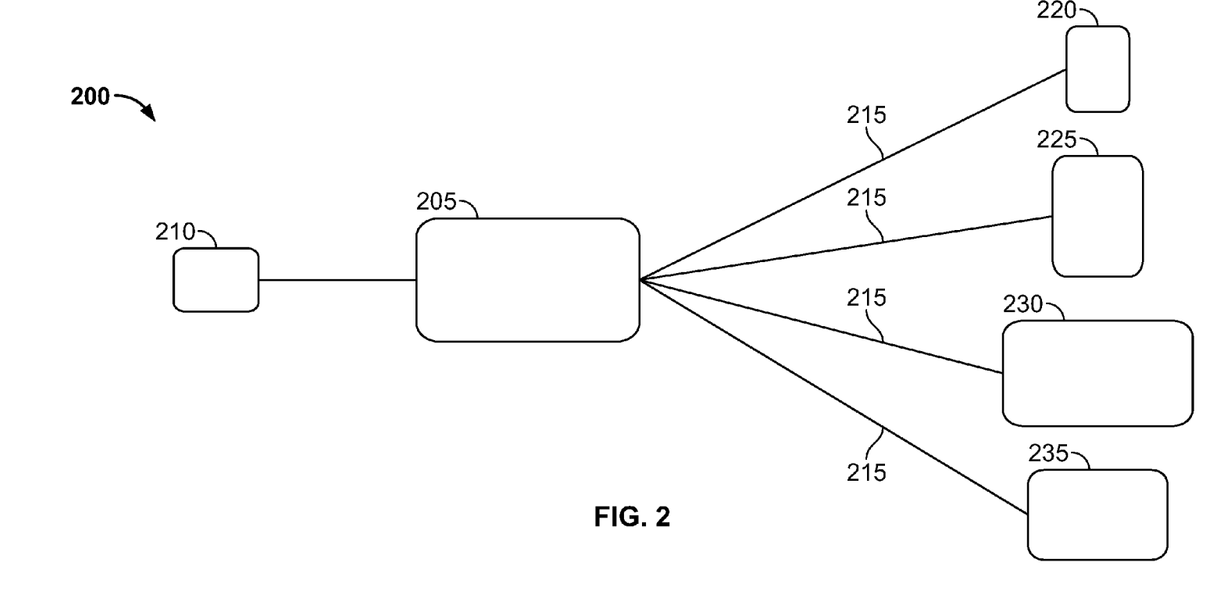
FIG. 2 is a block diagram illustrating another exemplary embodiment of the alarm priority system, depicting a bedside monitor with physiological parameter measurement device and four secondary alarming devices; and, FIG. 3 is a flow chart describing one exemplary embodiment of the alarm priority protocol.

In other embodiment, the alarm system can be coupled with more than one secondary device. FIG. 2 is a block diagram illustrating another exemplary embodiment of the alarm priority system 200 of the present invention, depicting a second computing device, such as a bedside monitor 205 further including a physiological parameter measurement device 210 and at least one first computing device, and preferably four first computing devices, such as, but not limited to secondary alarming devices 220, 225, 230, 235. Secondary alarming devices 220, 225, 230, 235 each include at least one of the following devices: a cellular phone, PDA, smartphone, tablet PC, other patient monitor, custom kiosk and/or any other computing device.

In one exemplary embodiment, first secondary device 220 is a cell phone, second secondary device 225 is a tablet PC, third secondary device 230 is a computer at a clinician's station, and fourth secondary device 240 is a custom display, such as a nurse's station kiosk. In other various embodiments, any combination of one or more of the secondary devices listed above, in addition to any other similar mobile or stationary device, can act as a secondary alarming device and assume primary alarm responsibility from the bedside monitor. These secondary devices are capable of generating both visual and audible alarms and are either carried by assigned caregivers or positioned in locations frequented by hospital personnel during the course of their work.

Communication between the bedside monitor 205 and the secondary devices 220, 225, 230, and 235 is maintained via a network connection 215. In one embodiment, data is transferred between the bedside monitor and the secondary device via a wired network. In another embodiment, data is transferred between the bedside monitor and the secondary device via a wireless network such as 802.11 a/b/g/n, Bluetooth, or other wireless communication protocol or standard. In another embodiment, data is transferred between the bedside monitor and the secondary device via a cellular network.

Figure 3:
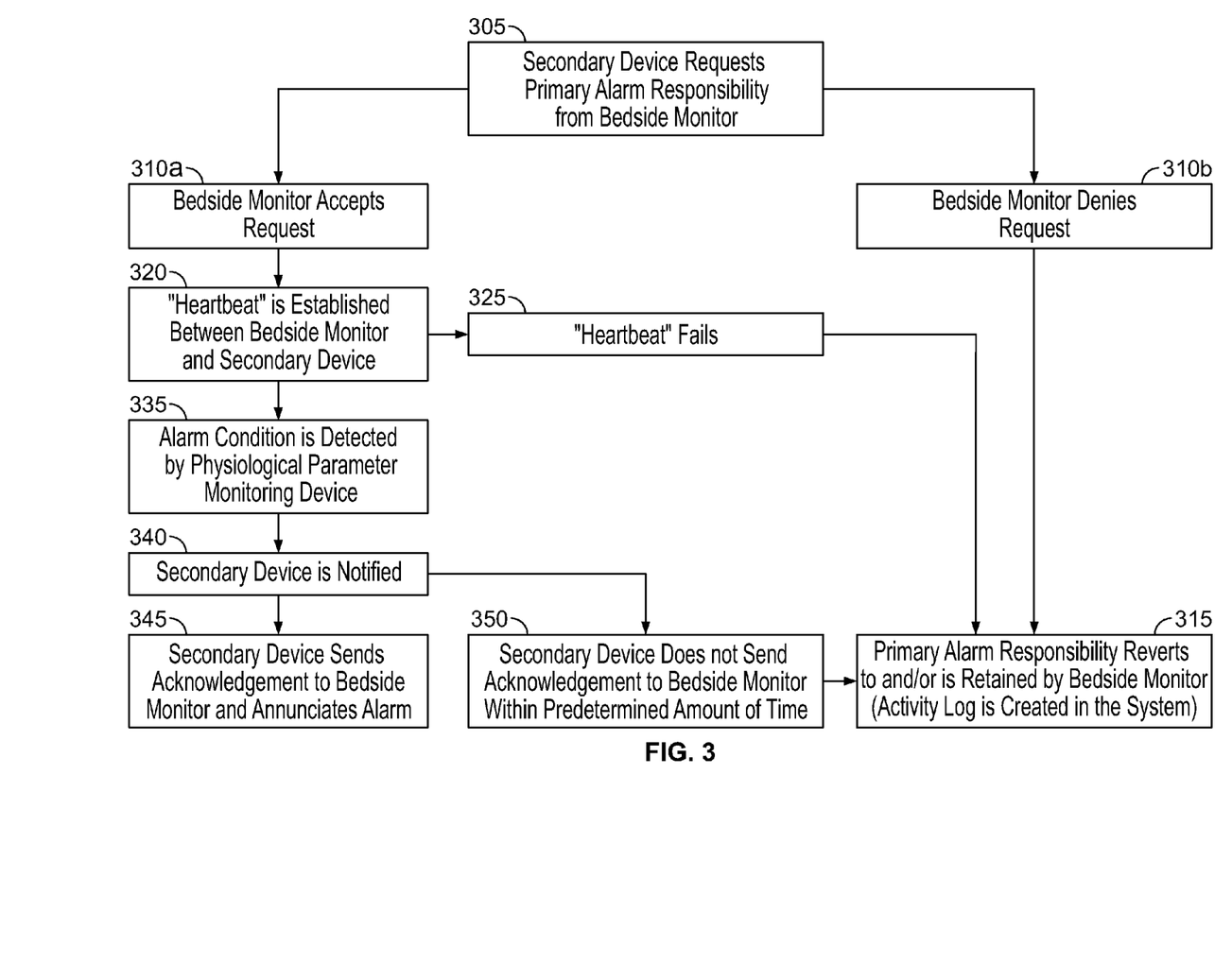

FIG. 3 is a flow chart describing one exemplary operational embodiment of the alarm priority process or protocol 300. In one embodiment, the bedside monitor delegates to, and retakes primary alarming responsibility from, the at least one secondary device through the following process, as described with respect to FIG. 3. The first computing system, a secondary alarming device, first requests in step 305, to become the primary alarming device for the monitoring system.

It should be appreciated that the request may be effectuated by the transmission of a message from an application executing in the first computing system (in one embodiment, a secondary device) to an application executing in the second computing system (in one embodiment, a bedside monitor). Each application is configured to receive, transmit, recognize, interpret, and process such request messages. It should further be appreciated that both the first and second computing systems, secondary device and monitoring system, respectively, have wireless and wired receivers and transmitters capable of sending and transmitting data, at least one processor capable of processing programmatic instructions, memory capable of storing programmatic instructions, and software comprised of a plurality of programmatic instructions for performing the processes described herein.

The second computing device or bedside monitor either accepts, in step 310a, or denies, in step 310b, the request from the first computing device or secondary alarming device in step 305. If denied, the bedside monitor retains, in step 315, primary alarming responsibility and the action is recorded in the activity log which is created in the system.

Referring back to FIG. 3, if a message formatted and transmitted from a secondary device is received and accepted in step 310a, by corresponding software executing in the bedside monitor, a connection is established, in step 320, by use of a "heartbeat", which is a predefined series of communications which are designed to confirm that the link between the monitor and secondary device is operational and that the secondary device is receiving, or capable of receiving, any alarm message sent by the bedside monitor. Both the bedside monitor and the secondary device have installed software that establishes the "heartbeat", or link, between the two devices. The "heartbeat" may be any series of messages, bits, codes, or other sequential, predefined set of transmitted data. Once established, the connection is maintained by the "heartbeat".

If the "heartbeat" connection fails at any time, in step 325, primary alarming responsibility is returned, in step 315, to the bedside monitor until such time as the "heartbeat" is re-established. A failed "heartbeat" generates a technical alarm notification on the secondary device and is logged by the system. In one embodiment, if the "heartbeat" fails, then the caregiver must manually re-establish a connection between the bedside monitor and the secondary device. In another embodiment, if the "heartbeat" fails, then a connection between the bedside monitor and secondary device can be established automatically by attempting to connect at predetermined time intervals until the caregiver aborts the connection process manually. In yet another embodiment, if the "heartbeat" fails, then the connection between the bedside monitor and secondary device can be established automatically by attempting to connect at predetermined time intervals until the maximum number of connection attempts is reached. It should be noted that the predetermined time interval for connection attempts and the maximum number of connection attempts can be programmed at the bedside monitor, the secondary device, or pre-programmed at point of manufacture.

Therefore, the bedside monitor remains the primary alarming device if the heartbeat between the bedside monitor and the secondary device fails to meet a pre-defined reliability threshold. If there is an intermittent "heartbeat" or an unreliable connection, the system will cease communication with the secondary device. In one embodiment, the system determines the number of connection interruptions and assesses whether the connection environment is reliable enough to allow a secondary device to assume alarm responsibility, based upon a pre-defined connection interruption threshold. In one embodiment, the number of acceptable connection interruptions or the connection interruption threshold is pre-programmed by the user at the bedside monitor. In another embodiment, the number of acceptable connection interruptions is pre-programmed at the point of manufacture and cannot be changed.

If the physiological monitoring device detects, in step 335, an alarm condition while primary alarming responsibility has been transferred to the at least one secondary device, the bedside monitor subsequently notifies, in step 340, the secondary device that an alarm condition is present by transmitting an alarm condition message from the bedside monitor to the secondary device. The alarm condition message may be any series of messages, bits, codes, or other sequential, pre-defined set of transmitted data that is recognized by both the bedside monitor and secondary device. It should further be appreciated that the alarm condition may contain different types of data, including just an indication that an alarm exists, data indicating the specific nature of the condition causing the alarm, and/or data indicating the severity of the alarm, among other data.

Once the secondary device receives the alarm message, it annunciates the alarm and sends an acknowledgement, in step 345, to the bedside monitor that the alarm is being presented on said secondary device. In one embodiment, the alarm annunciation is an audible alarm, such as a beep, ring, or other sound-based indicator. In one embodiment, the alarm annunciation is a visual alarm, such as a flashing light or status bar either on the secondary device itself or on the display of the secondary device, if available. In one embodiment, the alarm annunciation is audio-visual and can contain a plurality of indicators. In another embodiment, the alarm annunciation is customizable. In another embodiment, alarm annunciation can be customized in accordance with features available within the secondary device.

If the bedside monitor does not receive said acknowledgement within a predetermined period of time, in step 350, then primary alarming responsibility will revert to the bedside monitor, which, as in step 315, will assume primary alarm responsibility and is responsible for alarm annunciation. In one embodiment, the predetermined time period is programmable. In one embodiment, the predetermined time period is programmable at the bedside monitor using an application executing in the bedside monitor. In another embodiment, the predetermined time period is set at the point of manufacture.

In yet another embodiment, the predetermined time period is programmable at the secondary device using an application executing in the secondary device.

Figure 4:
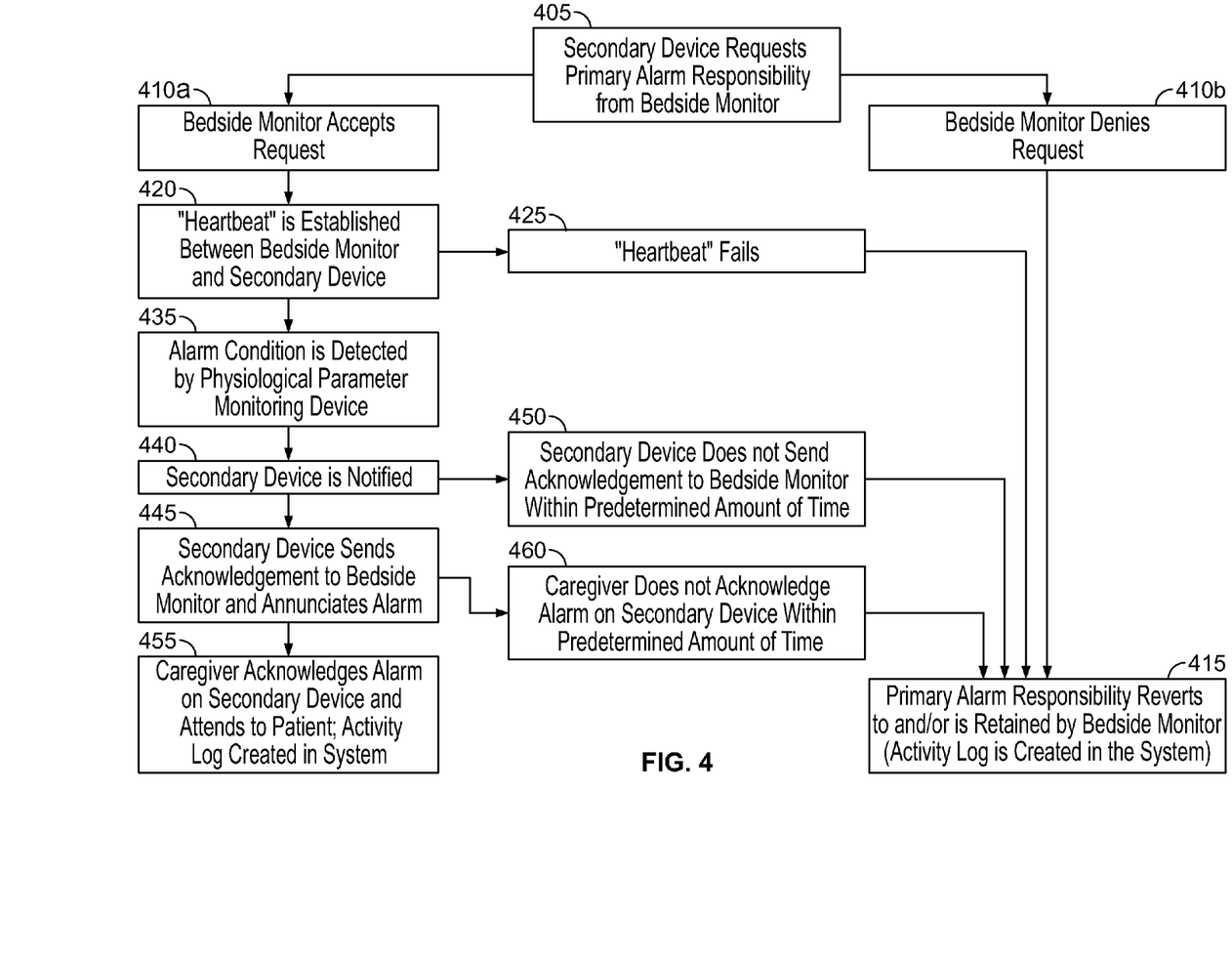
FIG. 4 is a flow chart describing another exemplary embodiment of the alarm priority protocol of the present invention including steps involving alarm recognition by a caregiver.

Optionally, in one embodiment, the alarm annunciated by the secondary device requires acknowledgement by the assigned caregiver. FIG. 4 is a flow chart describing another exemplary embodiment of the alarm priority protocol 400 including steps involving alarm recognition by a caregiver. In one optional embodiment, when the alarm is annunciated on the secondary device, a caregiver must acknowledge the alarm. In one embodiment, the caregiver acknowledges the alarm by pressing a key on the secondary device. In another embodiment, when the alarm is annunciated on the secondary device, a caregiver may speak into the device and issue a vocal command to acknowledge it. In another embodiment, a caregiver may select an acknowledgment button on a touchscreen display that is provided on the secondary device. In other embodiments, caregiver acknowledgment can take any form that is supported by the secondary device.

In one embodiment, acknowledging the alarm does not silence the alarm. Preferably, it causes a notification to the system, including the bedside monitor, that a caregiver has received and acknowledged the alarm.

In one embodiment, acknowledging the alarm by any method described above, or any other contemplated method, silences the alarm.

Referring now to FIG. 4, a secondary device requests, in step 405, to become the primary alarming device for the monitoring system. It should be appreciated that the request may be effectuated by the transmission of a message from an application executing in the first computing system (in one embodiment, a secondary device) to an application executing in the second computing system (in one embodiment, a bedside monitor). Each application is configured to receive, transmit, recognize, interpret, and process such request messages. It should further be appreciated that both the first and second computing systems, secondary device and monitoring system, respectively, have wireless and wired receivers and transmitters capable of sending and transmitting data, at least one processor capable of processing programmatic instructions, memory capable of storing programmatic instructions, and software comprised of a plurality of programmatic instructions for performing the processes described herein.

The second computing device or bedside monitor either accepts, in step 410*a*, or denies, in step 410*b*, the request from the first computing device or secondary alarming device in step 405. If denied, the bedside monitor retains, in step 415, primary alarming responsibility and the action is recorded in the activity log which is created in the system.

Referring back to FIG. 4, if a message formatted and transmitted from a secondary device is received and accepted in step 410*a*, by corresponding software executing in the bedside monitor, a connection is established, in step 420, by use of a "heartbeat", which is a predefined series of communications which are designed to confirm that the link between the monitor and secondary device is operational and that the secondary device is receiving, or capable of receiving, any alarm message sent by the bedside monitor. Both the bedside monitor and the secondary device have installed software that establishes the "heartbeat", or link, between the two devices. The "heartbeat" may be any series of messages, bits, codes, or other sequential, predefined set of transmitted data. Once established, the connection is maintained by the "heartbeat".

If the "heartbeat" connection fails at any time, in step 425, primary alarming responsibility is returned, in step 415, to the bedside monitor until such time as the "heartbeat" is re-established. A failed "heartbeat" generates a technical alarm notification on the secondary device and is logged by the system.

In one embodiment, if the "heartbeat" fails, then the caregiver must manually re-establish a connection between the bedside monitor and the secondary device. In another embodiment, if the "heartbeat" fails, then a connection between the bedside monitor and secondary device can be established automatically by attempting to connect at predetermined time intervals until the caregiver aborts the connection process manually. In yet another embodiment, if the "heartbeat" fails, then the connection between the bedside monitor and secondary device can be established automatically by attempting to connect at predetermined time intervals until the maximum number of connection attempts is reached. It should be noted that the predetermined time interval for connection attempts and the maximum number of connection attempts can be programmed at the bedside monitor, the secondary device, or pre-programmed at point of manufacture.

Therefore, the bedside monitor remains the primary alarming device if the heartbeat between the bedside monitor and the secondary device fails to meet a pre-defined reliability threshold. If there is an intermittent "heartbeat" or an unreliable connection, the system will cease communication with the secondary device. In one embodiment, the system determines the number of connection interruptions and assesses whether the connection environment is reliable enough to allow a secondary device to assume alarm responsibility, based upon a pre-defined connection interruption threshold. In one embodiment, the number of acceptable connection interruptions or the connection interruption threshold is pre-programmed by the user at the bedside monitor. In another embodiment, the number of acceptable connection interruptions is pre-programmed at the point of manufacture and cannot be changed.

If the physiological monitoring device detects, in step 435, an alarm condition while primary alarming responsibility has been transferred to the at least one secondary device, the bedside monitor subsequently notifies, in step 440, the secondary device that an alarm condition is present by transmitting an alarm condition message from the bedside monitor to the secondary device. The alarm condition message may be any series of messages, bits, codes, or other sequential, pre-defined set of transmitted data that is recognized by both the bedside monitor and secondary device. It should further be appreciated that the alarm condition may contain different types of data, including just an indication that an alarm exists, data indicating the specific nature of the condition causing the alarm, and/or data indicating the severity of the alarm, among other data.

If the bedside monitor does not receive said acknowledgement within a predetermined period of time, in step 450, then primary alarming responsibility will revert to the bedside monitor, which, as in step 415, will assume primary alarm responsibility and is responsible for alarm annunciation. In one embodiment, the predetermined time period is programmable. In one embodiment, the predetermined time period is programmable at the bedside monitor using an application executing in the bedside monitor. In another embodiment, the predetermined time period is set at the point of manufacture. In yet another embodiment, the predetermined time period is programmable at the secondary device using an application executing in the secondary device.

Once the secondary device receives the alarm message, it annunciates the alarm and sends an acknowledgement, in step 445, to the bedside monitor that the alarm is being presented on said secondary device. In one embodiment, the alarm annunciation is an audible alarm, such as a beep, ring, or other sound-based indicator. In one embodiment, the alarm annunciation is a visual alarm, such as a flashing light or status bar either on the secondary device itself or on the display of the secondary device, if available. In one embodiment, the alarm annunciation is audio-visual and can contain a plurality of indicators. In another embodiment, the alarm annunciation is customizable. In another embodiment, alarm annunciation can be customized in accordance with features available within the secondary device.

In step 455, when the alarm is annunciated on the secondary device, a caregiver must acknowledge the alarm on the secondary device and subsequently attends to the patient. If the caregiver does not acknowledge the alarm on the secondary device within a predetermined amount of time, in step 460, then primary alarming responsibility will revert to the bedside monitor, which, as in step 415, will assume primary alarm responsibility and is responsible for alarm annunciation. As mentioned above, the predetermined time period can be programmable or pre-set at the point of manufacture.

Thus, in one embodiment, a user prompt is generated, via a first plurality of programmatic instructions at the first computing device (secondary alarming device), so that the user can acknowledge receipt of an alarm message at the first computing device. The first plurality of programmatic instructions receives user input in response to the prompt generated to acknowledge receipt of an alarm message and transmits data indicative of said user input to the bedside monitor.

The alarm content, notification of the alarm by the bedside monitor, annunciation of the alarm by the secondary device, and acknowledgement of the alarm by the caregiver are all logged by the system.

In another embodiment, the bedside monitor can request that a secondary device take primary alarm responsibility, rather than the secondary device requesting primary alarm responsibility from the bedside monitor. For example, while a nurse is in the patient's room checking on the patient, the nurse indicates to the patient that the patient needs to sleep. The nurse then presses a "sleep" button on the monitor which results in the monitor presenting a list of known secondary devices that can take over primary alarm responsibility. At this point, the nurse selects one of the secondary devices and the patient monitor screen dims, goes blank, or otherwise darkens so as not to disturb the patient's sleep. The selected secondary device assumes primary alarm responsibility and then follows the same protocols as those listed above. If there are no secondary devices available, the bedside monitor retains primary alarm responsibility.

Figure 5:
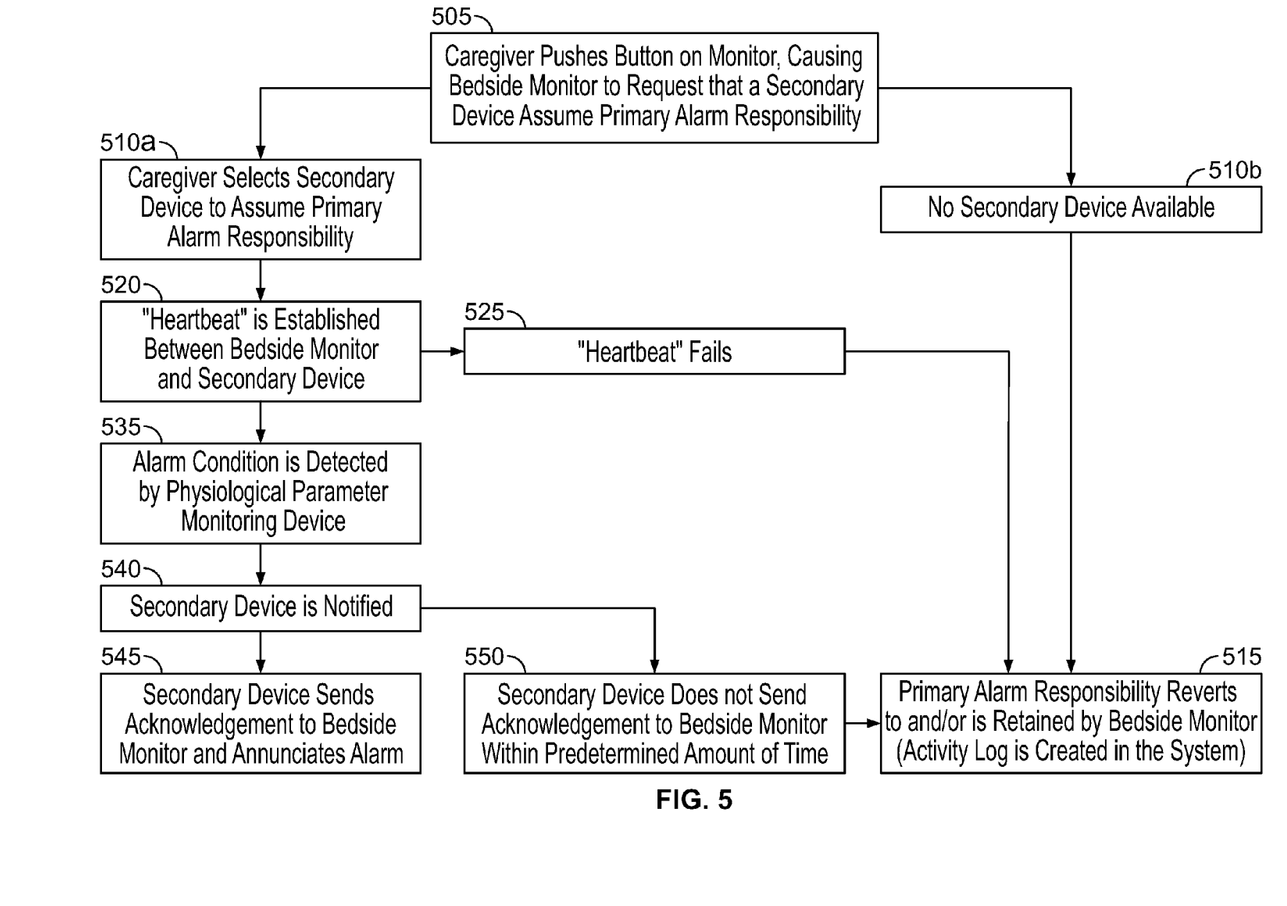
FIG. 5 is a flow chart describing another exemplary embodiment of the alarm priority protocol wherein the bedside monitor requests that a secondary device take primary alarm responsibility; and, FIG. 6 is a flow chart describing another exemplary embodiment of the alarm priority protocol wherein the bedside monitor requests that a secondary device take primary alarm responsibility, including steps involving alarm recognition by a caregiver.
Figure 6:
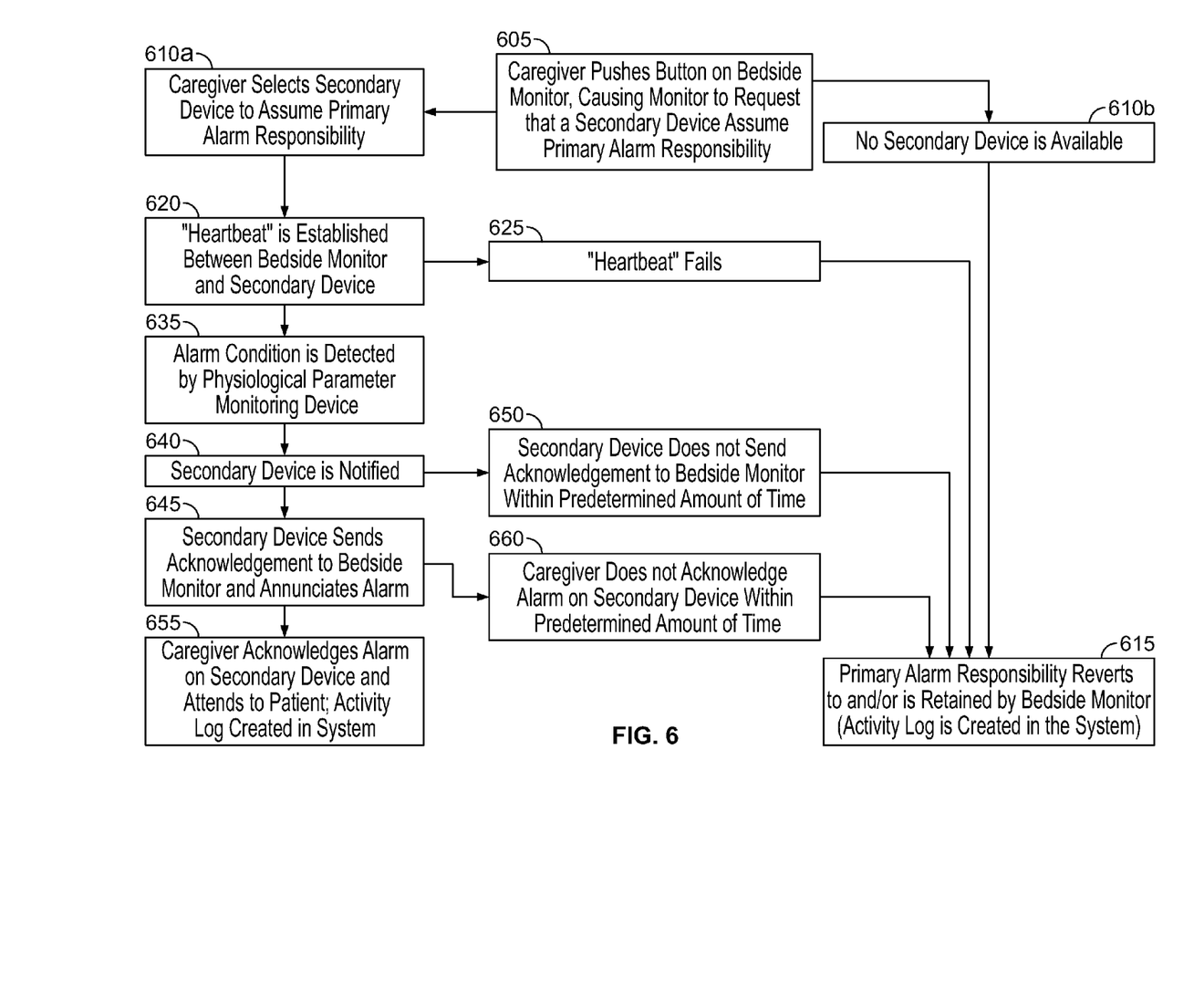

FIGS. 5 and 6 provide flow charts describing bedside monitor initiated embodiments of the alarm priority protocol 500, 600 of the present invention without and with the steps involving alarm recognition by a caregiver respectively.

FIG. 5 is a flow chart describing one exemplary operational embodiment of the alarm priority process or protocol 500. In one embodiment, the bedside monitor delegates to, and retakes primary alarming responsibility from, the at least one secondary device through the following process, as described with respect to FIG. 5. A caregiver, in step 305, pushes a button on the bedside monitor, causing the bedside monitor to request that a secondary device assume primary alarm responsibility for the monitoring system.

It should be appreciated that the request may be effectuated by the transmission of a message from an application executing in the first computing system (in one embodiment, a secondary device) to an application executing in the second computing system (in one embodiment, a bedside monitor). Each application is configured to receive, transmit, recognize, interpret, and process such request messages. It should further be appreciated that both the first and second computing systems, secondary device and monitoring system, respectively, have wireless and wired receivers and transmitters capable of sending and transmitting data, at least one processor capable of processing programmatic instructions, memory capable of storing programmatic instructions, and software comprised of a plurality of programmatic instructions for performing the processes described herein.

The caregiver selects, in step 510*a*, the secondary device to assume primary alarm responsibility. The caregiver, in one embodiment, can make this selection from the bedside monitor itself. In one embodiment, the selection is made from a drop-down menu (or other list type) of available devices. In one embodiment, the caregiver is required to enter a password corresponding to the selected device so that the device "pairs" with the bedside monitor. In another embodiment, the caregiver may select a device by "pairing" the device to the bedside monitor, using device pairing techniques that are well-known to those of ordinary skill in the art.

If no secondary device is available, as in 510*b*, the bedside monitor retains, in step 515, primary alarming responsibility and the action is recorded in the activity log which is created in the system.

Referring back to FIG. 5, if a message formatted and transmitted from a secondary device is received and accepted in step 510*a*, by corresponding software executing in the bedside monitor, a connection is established, in step 520, by use of a "heartbeat", which is a predefined series of communications which are designed to confirm that the link between the monitor and secondary device is operational and that the secondary device is receiving, or capable of receiving, any alarm message sent by the bedside monitor. Both the bedside monitor and the secondary device have installed software that establishes the "heartbeat", or link, between the two devices. The "heartbeat" may be any series of messages, bits, codes, or other sequential, predefined set of transmitted data. Once established, the connection is maintained by the "heartbeat".

If the "heartbeat" connection fails at any time, in step 525, primary alarming responsibility is returned, in step 515, to the bedside monitor until such time as the "heartbeat" is re-established. A failed "heartbeat" generates a technical alarm notification on the secondary device and is logged by the system.

In one embodiment, if the "heartbeat" fails, then the caregiver must manually re-establish a connection between the bedside monitor and the secondary device. In another embodiment, if the "heartbeat" fails, then a connection between the bedside monitor and secondary device can be established automatically by attempting to connect at predetermined time intervals until the caregiver aborts the connection process manually. In yet another embodiment, if the "heartbeat" fails, then the connection between the bedside monitor and secondary device can be established automatically by attempting to connect at predetermined time intervals until the maximum number of connection attempts is reached. It should be noted that the predetermined time interval for connection attempts and the maximum number of connection attempts can be programmed at the bedside monitor, the secondary device, or pre-programmed at point of manufacture.

Therefore, the bedside monitor remains the primary alarming device if the heartbeat between the bedside monitor and the secondary device fails to meet a pre-defined reliability threshold. If there is an intermittent "heartbeat" or an unreliable connection, the system will cease communication with the secondary device. In one embodiment, the system determines the number of connection interruptions and assesses whether the connection environment is reliable enough to allow a secondary device to assume alarm responsibility, based upon a pre-defined connection interruption threshold. In one embodiment, the number of acceptable connection interruptions or the connection interruption threshold is pre-programmed by the user at the bedside monitor. In another embodiment, the number of acceptable connection interruptions is pre-programmed at the point of manufacture and cannot be changed.

If the physiological monitoring device detects, in step 535, an alarm condition while primary alarming responsibility has been transferred to the at least one secondary device, the bedside monitor subsequently notifies, in step 540, the secondary device that an alarm condition is present by transmitting an alarm condition message from the bedside monitor to the secondary device. The alarm condition message may be any series of messages, bits, codes, or other sequential, pre-defined set of transmitted data that is recognized by both the bedside monitor and secondary device. It should further be appreciated that the alarm condition may contain different types of data, including just an indication that an alarm exists, data indicating the specific nature of the condition causing the alarm, and/or data indicating the severity of the alarm, among other data.

Once the secondary device receives the alarm message, it annunciates the alarm and sends an acknowledgement, in step 545, to the bedside monitor that the alarm is being presented on said secondary device. In one embodiment, the alarm annunciation is an audible alarm, such as a beep, ring, or other sound-based indicator. In one embodiment, the alarm annunciation is a visual alarm, such as a flashing light or status bar either on the secondary device itself or on the display of the secondary device, if available. In one embodiment, the alarm annunciation is audio-visual and can contain a plurality of indicators. In another embodiment, the alarm annunciation is customizable. In another embodiment, alarm annunciation can be customized in accordance with features available within the secondary device.

If the bedside monitor does not receive said acknowledgement within a predetermined period of time, in step 550, then primary alarming responsibility will revert to the bedside monitor, which, as in step 515, will assume primary alarm responsibility and is responsible for alarm annunciation. In one embodiment, the predetermined time period is programmable. In one embodiment, the predetermined time period is programmable at the bedside monitor using an application executing in the bedside monitor. In another embodiment, the predetermined time period is set at the point of manufacture. In yet another embodiment, the predetermined time period is programmable at the secondary device using an application executing in the secondary device.

Optionally, in one embodiment, the alarm annunciated by the secondary device requires acknowledgement by the assigned caregiver. FIG. 6 is a flow chart describing another exemplary embodiment of the alarm priority protocol 600 including steps involving alarm recognition by a caregiver. In one optional embodiment, when the alarm is annunciated on the secondary device, a caregiver must acknowledge the alarm. In one embodiment, the caregiver acknowledges the alarm by pressing a key on the secondary device. In another embodiment, when the alarm is annunciated on the secondary device, a caregiver may speak into the device and issue a vocal command to acknowledge it. In another embodiment, a caregiver may select an acknowledgment button on a touchscreen display that is provided on the secondary device. In other embodiments, caregiver acknowledgment can take any form that is supported by the secondary device.

In one embodiment, acknowledging the alarm does not silence the alarm. Preferably, it causes a notification to the system, including the bedside monitor, that a caregiver has received and acknowledged the alarm.

In one embodiment, acknowledging the alarm by any method described above, or any other contemplated method, silences the alarm.

In one embodiment, the bedside monitor delegates to, and retakes primary alarming responsibility from, the at least one secondary device through the following process, as described with respect to FIG. 6. A caregiver, in step 605, pushes a button on the bedside monitor, causing the bedside monitor to request that a secondary device assume primary alarm responsibility for the monitoring system.

It should be appreciated that the request may be effectuated by the transmission of a message from an application executing in the first computing system (in one embodiment, a secondary device) to an application executing in the second computing system (in one embodiment, a bedside monitor). Each application is configured to receive, transmit, recognize, interpret, and process such request messages. It should further be appreciated that both the first and second computing systems, secondary device and monitoring system, respectively, have wireless and wired receivers and transmitters capable of sending and transmitting data, at least one processor capable of processing programmatic instructions, memory capable of storing programmatic instructions, and software comprised of a plurality of programmatic instructions for performing the processes described herein.

The caregiver selects, in step 610*a*, the secondary device to assume primary alarm responsibility. The caregiver, in one embodiment, can make this selection from the bedside monitor itself. In one embodiment, the selection is made from a drop-down menu (or other list type) of available devices. In one embodiment, the caregiver is required to enter a password corresponding to the selected device so that the device "pairs" with the bedside monitor. In another embodiment, the caregiver may select a device by "pairing" the device to the bedside monitor, using device pairing techniques that are well-known to those of ordinary skill in the art.

If no secondary device is available, as in 610*b*, the bedside monitor retains, in step 615, primary alarming responsibility and the action is recorded in the activity log which is created in the system.

Referring back to FIG. 6, if a message formatted and transmitted from a secondary device is received and accepted in step 610*a*, by corresponding software executing in the bedside monitor, a connection is established, in step 620, by use of a "heartbeat", which is a predefined series of communications which are designed to confirm that the link between the monitor and secondary device is operational and that the secondary device is receiving, or capable of receiving, any alarm message sent by the bedside monitor. Both the bedside monitor and the secondary device have installed software that establishes the "heartbeat", or link, between the two devices. The "heartbeat" may be any series of messages, bits, codes, or other sequential, predefined set of transmitted data. Once established, the connection is maintained by the "heartbeat".

If the "heartbeat" connection fails at any time, in step 625, primary alarming responsibility is returned, in step 615, to the bedside monitor until such time as the "heartbeat" is re-established. A failed "heartbeat" generates a technical alarm notification on the secondary device and is logged by the system.

In one embodiment, if the "heartbeat" fails, then the caregiver must manually re-establish a connection between the bedside monitor and the secondary device. In another embodiment, if the "heartbeat" fails, then a connection between the bedside monitor and secondary device can be established automatically by attempting to connect at predetermined time intervals until the caregiver aborts the connection process manually. In yet another embodiment, if the "heartbeat" fails, then the connection between the bedside monitor and secondary device can be established automatically by attempting to connect at predetermined time intervals until the maximum number of connection attempts is reached. It should be noted that the predetermined time interval for connection attempts and the maximum number of connection attempts can be programmed at the bedside monitor, the secondary device, or pre-programmed at point of manufacture.

Therefore, the bedside monitor remains the primary alarming device if the heartbeat between the bedside monitor and the secondary device fails to meet a pre-defined reliability threshold. If there is an intermittent "heartbeat" or an unreliable connection, the system will cease communication with the secondary device. In one embodiment, the system determines the number of connection interruptions and assesses whether the connection environment is reliable enough to allow a secondary device to assume alarm responsibility, based upon a pre-defined connection interruption threshold. In one embodiment, the number of acceptable connection interruptions or the connection interruption threshold is pre-programmed by the user at the bedside monitor. In another embodiment, the number of acceptable connection interruptions is pre-programmed at the point of manufacture and cannot be changed.

If the physiological monitoring device detects, in step 635, an alarm condition while primary alarming responsibility has been transferred to the at least one secondary device, the bedside monitor subsequently notifies, in step 640, the secondary device that an alarm condition is present by transmitting an alarm condition message from the bedside monitor to the secondary device. The alarm condition message may be any series of messages, bits, codes, or other sequential, pre-defined set of transmitted data that is recognized by both the bedside monitor and secondary device. It should further be appreciated that the alarm condition may contain different types of data, including just an indication that an alarm exists, data indicating the specific nature of the condition causing the alarm, and/or data indicating the severity of the alarm, among other data.

If the bedside monitor does not receive said acknowledgement within a predetermined period of time, in step 650, then primary alarming responsibility will revert to the bedside monitor, which, as in step 615, will assume primary alarm responsibility and is responsible for alarm annunciation.

In one embodiment, the predetermined time period is programmable. In one embodiment, the predetermined time period is programmable at the bedside monitor using an application executing in the bedside monitor. In another embodiment, the predetermined time period is set at the point of manufacture. In yet another embodiment, the predetermined time period is programmable at the secondary device using an application executing in the secondary device.

Once the secondary device receives the alarm message, it annunciates the alarm and sends an acknowledgement, in step 645, to the bedside monitor that the alarm is being presented on said secondary device. In one embodiment, the alarm annunciation is an audible alarm, such as a beep, ring, or other sound-based indicator. In one embodiment, the alarm annunciation is a visual alarm, such as a flashing light or status bar either on the secondary device itself or on the display of the secondary device, if available. In one embodiment, the alarm annunciation is audio-visual and can contain a plurality of indicators. In another embodiment, the alarm annunciation is customizable. In another embodiment, alarm annunciation can be customized in accordance with features available within the secondary device.

In step 655, when the alarm is annunciated on the secondary device, a caregiver must acknowledge the alarm on the secondary device and subsequently attends to the patient. If the caregiver does not acknowledge the alarm on the secondary device within a predetermined amount of time, in step 660, then primary alarming responsibility will revert to the bedside monitor, which, as in step 615, will assume primary alarm responsibility and is responsible for alarm annunciation. As mentioned above, the predetermined time period can be programmable or pre-set at the point of manufacture.

Thus, in one embodiment, a user prompt is generated, via a first plurality of programmatic instructions at the first computing device (secondary alarming device), so that the user can acknowledge receipt of an alarm message at the first computing device. The first plurality of programmatic instructions receives user input in response to the prompt generated to acknowledge receipt of an alarm message and transmits data indicative of said user input to the bedside monitor.

The alarm content, notification of the alarm by the bedside monitor, annunciation of the alarm by the secondary device, and acknowledgement of the alarm by the caregiver are all logged by the system.

As discussed above, in various embodiments, multiple secondary devices are present on the system. In various embodiments, all of these multiple devices are selected as primary alarming devices. In various embodiments, with multiple secondary devices assuming primary alarming responsibility, multiple various protocols are available to determine alarming hierarchy within the group of secondary devices and between the secondary devices and the bedside monitor. In one embodiment, when an alarm condition arises, all secondary devices alarm and remain alarming until each is acknowledged by a caregiver. In another embodiment, when an alarm condition arises, all secondary devices alarm and remain alarming until one is acknowledged by a caregiver. In another embodiment, when an alarm condition arises, the secondary devices alarm sequentially in priority order if an alarm is presented but not acknowledged by a caregiver within a specific period of time. For all embodiments, the alarm content, notification of the alarm by the bedside monitor, annunciation of the alarm by the secondary devices, and acknowledgement of the alarm by the caregivers are all logged by the system.

In another embodiment, the secondary device acts as a redundant alarming device and also alarms when the primary device (bedside monitor alarms). This allows a caregiver to monitor patients remotely, but also notifies a caregiver that may be present in the room of an alarm condition. In this case, alarm acknowledgement can be effectuated by any device.

It should be clear to one familiar with the prior art, that a multitude of embodiments exist in which alarm notification hierarchy differs based on a multitude of possible protocols, and that the embodiments listed above are meant merely to be exemplary in nature and not all inclusive.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A system for managing alarms in a medical environment, comprising:
    a secondary device adapted to generate a request for primary alarm responsibility from a bedside monitor, establish a consistent confirmation that a communication link between the secondary device and the bedside monitor is operational, and, when an alarm condition is detected, actuate an alarm and send an acknowledgement to the bedside monitor; and
    the bedside monitor adapted to receive the request for primary alarm responsibility from the secondary device, establish said consistent confirmation that the communication link between the secondary device and the bedside monitor is operational, and, if said acknowledgement from the secondary device is not received in a predetermined amount of time, retake primary alarm responsibility from the secondary device.

2. The system of claim 1 wherein the bedside monitor is further configured to actuate an alarm if said acknowledgement from the secondary device is not received in a predetermined amount of time.

3. The system of claim 1 wherein the secondary device is further configured to receive an acknowledgement of the alarm by a user.

4. The system of claim 2 wherein the secondary device is further configured to communicate said acknowledgement of the alarm by the user to the bedside monitor.

5. The system of claim 4 wherein the bedside monitor is further configured to actuate an alarm if said acknowledgement of the alarm by the user is not received in a predetermined amount of time from the secondary device.

6. The system of claim 1 wherein, if the consistent confirmation that the communication link between the secondary device and the bedside monitor is operational is not detected by the bedside monitor, the bedside monitor retakes primary alarm responsibility from the secondary device.

7. The system of claim 1 wherein, if the consistent confirmation that the communication link between the secondary device and the bedside monitor is operational is not detected by the bedside monitor, the bedside monitor actuates said alarm.

8. The system of claim 1 wherein, if the consistent confirmation that the communication link between the secondary device and the bedside monitor is operational fails to meet a predefined reliability threshold, the bedside monitor retakes primary alarm responsibility from the secondary device.

9. The system of claim 1 wherein, if the consistent confirmation that the communication link between the secondary device and the bedside monitor is operational fails to meet a predefined reliability threshold, the bedside monitor actuates said alarm.

10. The system of claim 1 wherein said consistent confirmation that the communication link between the secondary device and the bedside monitor is an electronic heartbeat.

11. The system of claim 1 wherein said secondary device is at least one of a cellular phone, PDA, smart phone, tablet computing device, patient monitor, custom kiosk, or other computing device.

12. A system for managing alarms in a medical environment, comprising:
    a secondary device adapted to generate a request for primary alarm responsibility from a bedside monitor, establish an electronic heartbeat, said electronic heartbeat being a consistent confirmation that a communication link between the secondary device and the bedside monitor is operational, and, when an alarm condition is detected, actuate an alarm and send an acknowledgement to the bedside monitor; and the bedside monitor adapted to receive the request for primary alarm responsibility from the secondary device, establish said electronic heartbeat between the secondary device and the bedside monitor, and, if said acknowledgement from the secondary device is not received in a predetermined amount of time, actuate an alarm.

13. The system of claim 12 wherein the bedside monitor is further configured to retake primary alarm responsibility from the secondary device if said acknowledgement from the secondary device is not received in a predetermined amount of time.

14. The system of claim 12 wherein the secondary device is further configured to receive an acknowledgement of the alarm by a user.

15. The system of claim 14 wherein the secondary device is further configured to communicate said acknowledgement of the alarm by the user to the bedside monitor.

16. The system of claim 15 wherein the bedside monitor is further configured to actuate an alarm if said acknowledgement of the alarm by the user is not received in a predetermined amount of time from the secondary device.

17. The system of claim 12 wherein, if the electronic heartbeat is not detected by the bedside monitor, the bedside monitor retakes primary alarm responsibility from the secondary device.

18. The system of claim 12 wherein, if the electronic heartbeat is not detected by the bedside monitor, the bedside monitor actuates said alarm.

19. The system of claim 12 wherein, if the electronic heartbeat fails to meet a predefined reliability threshold, the bedside monitor retakes primary alarm responsibility from the secondary device.

20. The system of claim 12 wherein, if the electronic heartbeat fails to meet a predefined reliability threshold, the bedside monitor actuates said alarm.

* * * * *